United States Patent [19]

Somerville et al.

[11] Patent Number: 6,143,538
[45] Date of Patent: Nov. 7, 2000

[54] FATTY ACYL-COA REDUCTASE

[75] Inventors: Chris R. Somerville, Portola Valley, Calif.; Steven E. Reiser, University City, Mo.

[73] Assignee: The United States of America as represented by the United States Department of Energy, Washington, D.C.

[21] Appl. No.: 09/026,482

[22] Filed: Feb. 19, 1998

Related U.S. Application Data

[60] Provisional application No. 60/038,456, Feb. 20, 1997.

[51] Int. Cl.⁷ .............................. C12N 9/02; C12N 1/20; C12N 15/00; C07H 21/04; C07K 1/00
[52] U.S. Cl. .................. 435/189; 435/252.3; 435/320.1; 536/23.2; 536/23.7; 530/350
[58] Field of Search .................................. 435/189, 252.3, 435/320.1; 536/23.2, 23.7; 530/350

[56] References Cited

U.S. PATENT DOCUMENTS 5,411,879  5/1995  Pollard et al. .......................... 435/190

OTHER PUBLICATIONS

Reiser, Journal of Bacteriology, vol. 179(9): 2969–2975, May 1997.

*Primary Examiner*—Ponnathapu Achutamurthy
*Assistant Examiner*—Tekchand Saidha
*Attorney, Agent, or Firm*—Joy A. Alwan; Thomas G. Anderson; William R. Moser

[57] ABSTRACT

A bacterial gene which encodes an enzyme that is an acyl-CoA reductase. The acyl-CoA reductase is able to chemically reduce acyl-CoAs to their corresponding alcohols, via aldehyde intermediates.

16 Claims, 9 Drawing Sheets

```
CAG AAG ATA TGG TTC GGT TAT CGG TTG GGA TTG AAC ATA TTG ATG ATT TGA TTG CAG ATC    60
                                 oligo P5
TGG AAC AAG CAT TGG CCA CAG TTT GAG CGT AAA TTT TAT AAA AAA CCT CTG CAA TTT CAG   120

AGG TIT TIT TAT ATT TGC TTT ATT ATC GTA TGA TGT TCA TAA TTG ATC TAG CAA ATA ATA   180

AAA ATT AGA GCA ATT ACT CTA AAA ACA TTT GTA ATT TCA GAT ACT TAA CAC TAG ATT TTT   240
                             oligo P7
TAA CCA AAT CAC TTT AGA TTA ACT TTA GTT CTG GAA ATT TTA TTT CCC TTT AAC CGT CTT   300
                                                EcoRV
CAA TCC AAA TAC AAT AAT GAC AGC CTT TAC AGT TTG ATA TCA ATC AGG GAA AAA CGC GTG   360
                                                                            Met     1

AAC AAA AAA CTT GAA GCT CTC TTC CGA GAG AAT GTA AAA GGT AAA GTG GCT TTG ATC ACT   420
Asn Lys Lys Leu Glu Ala Leu Phe Arg Glu Asn Val Lys Gly Lys Val Ala Leu Ile Thr    21

GGT GCA TCT AGT GGA ATC GGT TTG ACG ATT GCA AAA AGA ATT GCT GCG GCA GGT GCT CAT   480
Gly Ala Ser Ser Gly Ile Gly Leu Thr Ile Ala Lys Arg Ile Ala Ala Ala Gly Ala His    41

GTA TTA TTG GTT GCC CGA ACC CAA GAA ACA CTG GAA GAA GTG AAA GCT GCA GGT GCT CAT   540
Val Leu Leu Val Ala Arg Thr Gln Glu Thr Leu Glu Glu Val Lys Ala Ala Ile Glu Gln    61

CAA GGG GGA CAG GCC TCT ATT TTT CCT TGT GAC CTG ACT GAC ATG AAT GCG ATT GAC CAG   600
Gln Gly Gly Gln Ala Ser Ile Phe Pro Cys Asp Leu Thr Asp Met Asn Ala Ile Asp Gln    81

TTA TCA CAA CAA ATT ATG GCC AGT GTC GAT CAT GTC GAT TTC CTG ATC AAT AAT CGA GGG   660
Leu Ser Gln Gln Ile Met Ala Ser Val Asp His Val Asp Phe Leu Ile Asn Asn Ala Gly   101

CGT TCG ATT CGC CGT GCC GTA CAC GAG TCG TTT GAT CGC TTC CAT GAT TTT GAA CGC ACC   720
Arg Ser Ile Arg Arg Ala Val His Glu Ser Phe Asp Arg Phe His Asp Phe Glu Arg Thr   121

ATG CAG CTG AAT TAC TTT GGT GCG GTA CGT TTA GTG TTA AAT TTA CTG CCA CAT ATG ATT   780
Met Gln Leu Asn Tyr Phe Gly Ala Val Arg Leu Val Leu Asn Leu Leu Pro His Met Ile   141

AAG CGT AAA AAT GGC CAG ATC ATC AAT ATC AGC TCT ATT GGT GTA TTG GCC AAT GCG ACC   840
Lys Arg Lys Asn Gly Gln Ile Ile Asn Ile Ser Ser Ile Gly Val Leu Ala Asn Ala Thr   161

CGT TTT TCT GCT TAT GTC GCG TCT AAA GCT GCG CTG GAT GCC TTC AGT CGC TGT CTT TCA   900
Arg Phe Ser Ala Tyr Val Ala Ser Lys Ala Ala Leu Asp Ala Phe Ser Arg Cys Leu Ser   181

GCC GAG GTA CTC AAG CAT AAA ATC TCA ATT ACC TCG ATT TAT ATG CCA TTG GTG CGT ACC   960
Ala Glu Val Leu Lys His Lys Ile Ser Ile Thr Ser Ile Tyr Met Pro Leu Val Arg Thr   210

CCA ATG ATC GCA CCC ACC AAA ATT TAT AAA TAC GTG CCC ACG CTT TCC CCA GAA GAA GCC  1020
Pro Met Ile Ala Pro Thr Lys Ile Tyr Lys Tyr Val Pro Thr Leu Ser Pro Glu Glu Ala   221

GCA GAT CTC ATT GTC TAC GCC ATT GTG AAA CGT CCA ACA CGT ATT GCG ACG CAC TTG GGT  1080
Ala Asp Leu Ile Val Tyr Ala Ile Val Lys Arg Pro Thr Arg Ile Ala Thr His Leu Gly   241
                                            FIG. 3
```

```
CGT CTG GCG TCA ATT ACC TAT GCC ATC GCA CCA GAC ATC AAT AAT ATT CTG ATG TCG ATT    1140
Arg Leu Ala Ser Ile Thr Tyr Ala Ile Ala Pro Asp Ile Asn Asn Ile Leu Met Ser Ile     261

GGA TTT AAC CTA TTC CCA AGC TCA ACG GCT GCA CTG GGT GAA CAG GAA AAA TTG AAT CTG    1200
Gly Phe Asn Leu Phe Pro Ser Ser Thr Ala Ala Leu Gly Glu Gln Glu Lys Leu Asn Leu     281

CTA CAA CGT GCC TAT GCC CGC TTG TTC CCA GGC GAA CAC TGG TAA AAT TTA TAA AAG AAG    1260
Leu Gln Arg Ala Tyr Ala Arg Leu Phe Pro Gly Glu His Trp                             295

CCT CTC ATA CCG AGA GGC TTT TTT ATG GTT ACG ACC ATC AGC CAG ATT TAG AGG AAA TTG    1320

ACT TTT CCT GTT TTT ACA TCA TAA ATC GCA CCA ACA ATA TCA ATT TCT TTG CGA TCC AGC    1380

ATA TCT TTA AGT ACA GAA CTA TGC TGA ATA ATG TAT TGA ATA TTA TAG TGA ACA TTC ATA    1380

ATA TCT TTA AGT ACA GAA CTA TGC TGA ATA ATG TAT TGA ATA TTA TAG TGA ACA TTC ATA    1440

GCA GTC ACC TGA TCA ATA AAT GCT TTG CTT AAT TCA CGC GGT TGC ATA ATA TCA AAT ACA    1500

CTG CCA ACC GAA TGC ATG AGT GGC CCA AGC ACG TAT TGG ATG TGT GGC ATT TCC TGA ATA    1560

TCG GAA ATC TGC TTA TGT TGC AAT CTT AAV TGG CAT GCG CTG GTG ACC GCA CCA CAG TCG    1620

GTA TGT CCC AAA ACC AGA ATC ACT TTG GAA CCT TTG TGA GCT CAG GCA AA                 1670
```

FIG. 3 (continued)

```
                    10         20         30         40         50         60
Acr1.AMI    VNKKLEALFRENVKGKVALITGASSGIGLTIAKRIAAAGAHVLLVARTQETLEEVKAAIE
             .         .   .. .........        .     ..  ..  ..  ....  . .    .
             .      . .. ............       .   ..  .. ..  .  ....... ...
ORF2.AMI    HLDPDRARRNDPLLGRHVIITGASSGIGRASAIAVAKRGATVFALARNGNALDELVTEIR
                    80         90        100        110        120        130

70         80         90        100        110        120
Acr1.AMI    QQGGQASIFPCDLTDMVAIDQLSQQIMASVDHVDFLINNAGRSIRRAVHESFDRFHDEFR
             ....  . ... ..         .    ....  ..........  . .. .. ..
             ....... ........  .....  ......  .....................  .. .........
ORF2.AMI    AHGGQAHAFTCDVTDSASVEHTVKDILGRFDHVDYLVNNAGRSIRRSVVNSTDRLHDYER
                   140        150        160        170        180        190

130        140        150        160        170        180
Acr1.AMI    TMQLNYFGAVRLVLNLLPHMIKRKNGQIINISSIGVLANATRFSAYVASKAALDAFSRCL
              .  .......  . ....    .    .    ..   ..   . .  .  .......
              ....................   ...    . .  ..  .. ..      .     .
ORF2.AMI    VMAVNYFGAVRMVLALLPHWRERRFGHVVNVSSAGVQARNPKYSSYLPTKAALDAFADVV
                   200        210        220        230        240        250

190        200        210        220        230        240
Acr1.AMI    SAEVLKHKISITSIYMPLVRTPMIAPTKIYKYVPTLSPEEAADLIVYAIVKRPTRIATHL
              .  .   . . . ....  ....       .    .   .   . .    .  .....
              ... . ... ... .. ..         .  ..........   ..  ..............
ORF2.AMI    ASETLSDHITFTNIHMPLVATPMIVPSRRLNPVRAISRERAAAMVIRGLVEKPARIDTPL
                   260        270        280        290        300        310

250        260        270        280        290
Acr1.AMI    GRLASITYAIAPDINNILMSIGFNLFPSSTAALGEQEKLNLLQRAYARLFPGEHW
             . ..       ..              . . .              .  .
             . ... .  ... ... ..   .........  .                 . .
ORF2.AMI    GTLAEAGNYVAPRLSRRILHQLYGYPDSAAAQGISRPDAADRPPAPRRPRRSARA
                   320        330        340        350        360
```

FIG. 5

```
             10        20        30        40        50        60
ACR1    LEALFRENVKGKVALITGASSGIGLTIAKRIAAAGAHVLLVARTQETLEEVKAAIEQQGG
          .         ....   .     ...   .     .  . .       .       .
         ..   ..  ...............  ............  ...  ...  ..........  .  .....  .
T21872  MEKKLPRRLEGKVAIVTASTQGIGFGITERFGLEGASVVVSSRKQANVDEAVAKLKSKGI
             10        20        30        40        50        60

70        80        90       100
ACR1    QASIFPCDLTDMNAIDQLSQQIMASVDHVDFLINNAGR
          .   .           .             .   ..
         ..  . ......  .    ..  .......  ........  ...
T21872  DAYGIVCHVSNAQHRRNLVEKTVQKYGKIDIVVCNAAA
             70        80        90
```

FIG. 7

```
                 20         30         40         50         60         70
ACR1      KVALITGASSGIGLTIAKRIAAAGAHVLLVARTQETLEEVKAAIEQQGGQASIFPCDLTD
           ..  ...  ....  .      .  ..       .      .       . . .   .. .
           ............  ....  ...  ....  .  ...  ...   .  ....  ...   .....
Z27263    MTALVTGAASGIGYAIVEELAGFGARIHVCDISETLLNQSLREWEKKGFQVSGSVCDVTS
             10         20         30         40         50         60

80         90         100        110        120
ACR1      MVAIDQLSQQIMASVD-HVDFLINNAGRSIRRAVHESF-DRFHDFERTMQL
           ..    .    .  ..........          . .          .
           ... ...   . ..........        .        . . .      .
Z27263    RPEREKLMQTVSSLFDGKLNILVNNVGVLRAKPTTEYVADDFTFHISTNL
                 70         80         90        100        110
```

FIG. 8

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 1670 base pairs
      (B) TYPE: nucleic acid
      (C) STRANDEDNESS: double
      (D) TOPOLOGY: linear (ii) MOLECULE TYPE: DNA (genomic)

(xi) SEQUENCE DESCRIPTION: SEQ ID NO:1:

```
CAGAAGATAT GGTTCGGTTA TCGGTTGGGA TTGAACATAT TGATGATTTG ATTGCAGATC      60
TGGAACAAGC ATTGGCCACA GTTTGAGCGT AAATTTTATA AAAAACCTCT GCAATTTCAG     120
AGGTTTTTTT ATATTTGCTT TATTATCGTA TGATGTTCAT AATTGATCTA GCAAATAATA     180
AAAATTAGAG CAATTACTCT AAAAACATTT GTAATTTCAG ATACTTAACA CTAGATTTTT     240
TAACCAAATC ACTTTAGATT AACTTTAGTT CTGGAAATTT TATTTCCCTT TAACCGTCTT     300
CAATCCAAAT ACAATAATGA CAGCCTTTAC AGTTTGATAT CAATCAGGGA AAAACGCGTG     360
AACAAAAAAC TTGAAGCTCT CTTCCGAGAG AATGTAAAAG GTAAAGTGGC TTTGATCACT     420
GGTGCATCTA GTGGAATCGG TTTGACGATT GCAAAAAGAA TTGCTGCGGC AGGTGCTCAT     480
GTATTATTGG TTGCCCGAAC CCAAGAAACA CTGGAAGAAG TGAAAGCTGC AATTGAACAG     540
CAAGGGGAC AGGCCTCTAT TTTTCCTTGT GACCTGACTG ACATGAATGC GATTGACCAG      600
TTATCACAAC AAATTATGGC CAGTGTCGAT CATGTCGATT TCCTGATCAA TAATGCAGGG     660
CGTTCGATTC GCCGTGCCGT ACACGAGTCG TTTGATCGCT TCCATGATTT TGAACGCACC     720
ATGCAGCTGA ATTACTTTGG TGCGGTACGT TTAGTGTTAA ATTTACTGCC ACATATGATT     780
AAGCGTAAAA ATGGCCAGAT CATCAATATC AGCTCTATTG GTGTATTGGC CAATGCGACC     840
CGTTTTTCTG CTTATGTCGC GTCTAAAGCT GCGCTGGATG CCTTCAGTCG CTGTCTTTCA     900
GCCGAGGTAC TCAAGCATAA AATCTCAATT ACCTCGATTT ATATGCCATT GGTGCGTACC     960
CCAATGATCG CACCCACCAA AATTTATAAA TACGTGCCCA CGCTTTCCCC AGAAGAAGCC    1020
GCAGATCTCA TTGTCTACGC CATTGTGAAA CGTCCAACAC GTATTGCGAC GCACTTGGGT    1080
CGTCTGGCGT CAATTACCTA TGCCATCGCA CCAGACATCA ATAATATTCT GATGTCGATT    1140
GGATTTAACC TATTCCCAAG CTCAACGGCT GCACTGGGTG AACAGGAAAA ATTGAATCTG    1200
CTACAACGTG CCTATGCCCG CTTGTTCCCA GGCGAACACT GGTAAAATTT ATAAAAGAAG    1260
CCTCTCATAC CGAGAGGCTT TTTTATGGTT ACGACCATCA GCCAGATTTA GAGGAAATTG    1320
ACTTTTCCTG TTTTTACATC ATAAATCGCA CCAACAATAT CAATTTCTTT GCGATCCAGC    1380
ATATCTTTAA GTACAGAACT ATGCTGAATA ATGTATTGAA TATTATAGTG AACATTCATA    1440
GCAGTCACCT GATCAATAAA TGCTTTGCTT AATTCACGCG GTTGCATAAT ATCAAATACA    1500
CTGCCAACCG AATGCATGAG TGGCCCAAGC ACGTATTGGA TGTGTGGCAT TTCCTGAATA    1560
TCGGAAATCT GCTTATGTTG CAATCTTAAC TGGCATGCGC TGGTGACCGC ACCACAGTCG    1620
GTATGTCCCA AAACCAGAAT CACTTTGGAA CCTTTGGCTT GACAGGCAAA               1670
```

(2) INFORMATION FOR SEQ ID NO:2:

```
     (i) SEQUENCE CHARACTERISTICS:
         (A) LENGTH: 295 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:2:

Met Asn Lys Lys Leu Glu Ala Leu Phe Arg Glu Asn Val Lys Gly Lys
 1               5                  10                  15

Val Ala Leu Ile Thr Gly Ala Ser Ser Gly Ile Gly Leu Thr Ile Ala
            20                  25                  30

Lys Arg Ile Ala Ala Ala Gly Ala His Val Leu Leu Val Ala Arg Thr
            35                  40                  45

Gln Glu Thr Leu Glu Glu Val Lys Ala Ala Ile Glu Gln Gln Gly Gly
    50                  55                  60

Gln Ala Ser Ile Phe Pro Cys Asp Leu Thr Asp Met Asn Ala Ile Asp
65                  70                  75                  80

Gln Leu Ser Gln Gln Ile Met Ala Ser Val Asp His Val Asp Phe Leu
                85                  90                  95

Ile Asn Asn Ala Gly Arg Ser Ile Arg Arg Ala Val His Glu Ser Phe
                100                 105                 110

Asp Arg Phe His Asp Phe Glu Arg Thr Met Gln Leu Asn Tyr Phe Gly
            115                 120                 125

Ala Val Arg Leu Val Leu Asn Leu Leu Pro His Met Ile Lys Arg Lys
            130                 135                 140

Asn Gly Gln Ile Ile Asn Ile Ser Ser Ile Gly Val Leu Ala Asn Ala
145                 150                 155                 160

Thr Arg Phe Ser Ala Tyr Val Ala Ser Lys Ala Ala Leu Asp Ala Phe
                165                 170                 175

Ser Arg Cys Leu Ser Ala Glu Val Leu Lys His Lys Ile Ser Ile Thr
            180                 185                 190

Ser Ile Tyr Met Pro Leu Val Arg Thr Pro Met Ile Ala Pro Thr Lys
        195                 200                 205

Ile Tyr Lys Tyr Val Pro Thr Leu Ser Pro Glu Glu Ala Ala Asp Leu
    210                 215                 220

Ile Val Tyr Ala Ile Val Lys Arg Pro Thr Arg Ile Ala Thr His Leu
225                 230                 235                 240

Gly Arg Leu Ala Ser Ile Thr Tyr Ala Ile Ala Pro Asp Ile Asn Asn
                245                 250                 255

Ile Leu Met Ser Ile Gly Phe Asn Leu Phe Pro Ser Ser Thr Ala Ala
                260                 265                 270

Leu Gly Glu Gln Glu Lys Leu Asn Leu Leu Gln Arg Ala Tyr Ala Arg
            275                 280                 285

Leu Phe Pro Gly Glu His Trp
            290                 295
```

FATTY ACYL-COA REDUCTASE

This application claims the benefit of U.S. Provisional Application No. 60/038456, filed Feb. 20, 1997.

This work was supported by a grant (#DE-FG02-94ER20133) from the United States Department of Energy. The Government has certain rights in the invention.

BACKGROUND OF THE INVENTION

1. Field of the Invention

The present invention relates to bacterial enzymes, in particular to an acyl-CoA reductase and a gene encoding an acyl-CoA reductase, the amino acid and nucleic acid sequences corresponding to the reductase polypeptide and gene, respectively, and to methods of obtaining such enzymes, amino acid sequences and nucleic acid sequences. The invention also relates to the use of such sequences to provide transgenic host cells capable of producing fatty alcohols and fatty aldehydes.

2. Background Information

Fatty acids are organic acids which are present in lipids, and vary in carbon content from $C_2$ to $C_{34}$. In biosynthetic reactions, they are often covalently bound through a thioester linkage to Coenzyme A (CoA) to form acyl-CoA or to acyl carrier proteins (ACPs) to form acyl-ACP. Fatty acids serve numerous physiological functions. For example, they may be joined through an ester linkage to fatty alcohols to form waxes, and to glycerol molecules through ester linkages to form triglycerides.

Linear wax esters are lipophilic compounds containing a long chain fatty alcohol esterified to a long chain fatty acid. In naturally occurring wax esters, the fatty alcohol and fatty acid moieties typically each contain 16 to 24 carbons and may contain one or more unsaturations. Such wax esters are found in a number of different organisms. For instance, wax esters are the principal component of spermaceti oil which, until recently, was obtained from the head cavity of sperm whales (*Physeter macrocephalus*). In 1979 the United states banned the import of all cetacean products and in 1982 the European Community enacted similar legislation. Since this time, the only natural source of wax esters on a commercial scale has been the seeds of jojoba (*Simmondsia chinensis* Link), a bush or shrub that is adapted to growth in hot arid habitats. In jojoba, waxes are stored in the seeds of the plant where they serve as a means of energy storage for developing seedlings. Wax esters have also been found in several species of bacteria such as *Acinetobacter calcoaceticus*, a gram negative aerobic bacteria that accumulates wax esters when grown under nitrogen limited conditions (Fixter et al.1986). Although these organisms are very diverse, examination of the chemical structures of the waxes they produce reveals that these waxes are very similar to each other structurally, in terms of their fatty acid and fatty alcohol components, carbon chain lengths and degree of saturation.

Wax esters have important commercial applications in a variety of technical areas, including the medical, cosmetics and food industries as well as their more traditional usage as lubricants for mechanical parts and the like. Consequently, enzymes and enzymatic pathways which are involved in production of waxes have great potential utility for more efficient production of known waxes, as well as for production of useful novel compounds.

Likewise, fatty alcohols and aldehydes have important commercial uses, e.g. as solvents, lubrication oil additives, plasticizers, nonionic surfactants, in pharmaceutical compositions as salves and lotions and as ingredients in cosmetics.

The wax esters obtained from jojoba can replace sperm whale oil in most or all traditional uses. They are useful for applications in cosmetics, as a lubricant, as an additive for leather processing, as a carrier for pharmaceuticals and as a solvent. Hydrogenation of the wax to eliminate double bonds produces a hard wax which is useful for surface treatments, in textile sizing, in coating paper containers and in cosmetics (eg., lipstick and creams). Sulphurization of the wax or other modifications make the substance useful in specialty lubricant applications, as a textile softener, as a component of printing inks, and as a component in many technical products such as corrosion inhibitors, surfactants, detergents, disinfectants, plasticizers, resins and emulsifiers. For some of these applications the fatty alcohol derived by hydrolysis of the wax ester is the most valuable ingredient derived from the wax ester. However, because the yield of the jojoba plant is relatively low, the oil is relatively expensive compared with edible oils from plants or technically comparable materials from petroleum. Thus, there has been interest in developing an alternate biological source of wax esters and long-chain alcohols. One possibility, in this respect, is to modify a microbial species for efficient production of wax esters or long-chain alcohols. Another possibility is to transfer the capability to produce wax esters or long-chain fatty alcohols to highly productive plant species.

Acyl-CoA compounds are utilized as substrates by fatty acyl reductases to form primary fatty alcohols in a two step process in which aldehydes are intermediate products. The alcohol product can then be joined through an ester linkage to a fatty acid to form a wax. Thus, fatty acyl reductases are involved in the production of fatty alcohols, aldehydes and wax esters.

The most detailed published information concerning wax ester biosynthesis concerns wax biosynthesis in jojoba where it appears that two enzymes catalyze the formation of wax esters (Pollard and Metz 1995; Metz et al. 1995). The first step of the pathway is catalyzed by a fatty acyl-CoA reductase which is highly substrate-specific for tetracosenoyl-CoA (a 24 carbon acyl-CoA), and is known to catalyze the formation of a long chain alcohol directly from this substrate via an aldehyde intermediate (Pollard and Metz 1995). The second enzyme,an acyl-CoA-fatty alcohol transferase catalyzes the formation of an ester linkage between acyl-CoA and a fatty alcohol to yield a wax ester. Assays on this enzyme, found it to be acyl-CoA specific, preferring $C_{20}$-monounsaturated acyl-CoA's and $C_{14}$ and $C_{18}$ mono- and di-unsaturated fatty alcohols (Metz et al. 1995).

Relatively little is known in detail about the biochemical mechanisms of wax ester production in bacteria. It is generally believed that the starting substrate is either acyl-ACP or acyl-CoA. The acyl compound is thought to be reduced to the corresponding aldehyde by an acyl-ACP or acyl-CoA reductase. An aldehyde intermediate has been proposed to occur based on the observation of a constitutive NADdependent long chain alkanal dehydrogenase and an inducible (induced in the presence of alkanes) NADP-dependent alkanal dehydrogenase in crude extracts of Acinetobacter strain HO1-N (Fox et al. 1992; Singer and Finnerty 1985c). With this observed activity from these two enzymes, it was proposed that one, or both, of the enzymes might be catalyzing the reverse reaction, reducing acyl-ACP to the corresponding aldehyde. However, no direct evidence was put forth to support this idea. The second step in wax ester formation involves the reduction of the fatty aldehyde to its corresponding fatty alcohol. Here again, the same logic was proposed. Two independent reports describe cofactor dependent and independent fatty alcohol dehydrogenases which have been proposed to play a role in wax ester biosynthesis (Fox et al. 1992; Singer and Finnerty 1985b). However, these reports are based on the use of crude extracts which may contain many different enzymes of similar function. Thus, nothing about the relevant enzymes is known with any degree of certainty based on previous published studies.

Several U.S. patents disclose fatty acyl reductase proteins isolated from plants.

U.S. Pat. No. 5,403,918 describes a partially purified fatty acyl reductase protein produced from jojoba embryos with activity towards acyl substrates having chain lengths from 16 to 24 carbon atoms. This enzyme is NADPH dependent, has a molecular mass of about 53 kD, and prefers very long chain acyl-CoA substrates.

U.S. Pat. No. 5,411,879 discloses partially purified proteins of about 32 kD and 47 kD obtained from jojoba embryos which are proposed to be components of an NADPH-dependent fatty acyl-CoA reductase, and two short amino acid sequences obtained from the 47 kD protein.

U.S. Pat. No. 5,370,996 discloses the nucleic acid sequence and translated amino acid sequence of a jojoba fatty acyl reductase.

From the limited amount of information available about the fatty acyl reductases from jojoba it appears that the enzyme has a strong substrate preference for acyl groups of 20 carbons or more in length. By contrast, the fatty acyl reductase from A. calcoaceticus appears to preferentially utilize shorter chain fatty acyl substrates. Growth of cultures in minimal mineral media with succinate or acetate as a carbon source produced wax esters in which about 50% were composed of two 16 carbon acyl groups and another 40% had one 16 carbon acyl group (Dewitt et al. 1982). By growing the bacteria in minimal mineral media with hexadecane (a 16 carbon alkane) as a carbon source 100% of the waxes were 32 carbons in length. Incubation of cultures in longer chain alkanes was found to give rise to wax ester compositions of $C_{2n}$, $C_{2n-2}$ and $C_{2n-4}$ (Dewitt et al. 1982). Thus, the availability of genes encoding the bacterial enzyme may permit the production of fatty alcohols and wax esters of different chemical composition than the jojoba enzyme. Also, since it is not known what regulates the activity of fatty acyl reductases, the bacterial enzymes described here may have different mechanisms of regulation than the jojoba enzyme. It is also shown that the enzymes of this invention are closely related to an enzyme that participates in the formation of mycolic acid, a lipophilic constituent of the human pathogen Mycobacterium tuberculosis. Thus, the detailed information concerning the genes and enzymes of this invention may be used to facilitate the design of new drugs that inhibit the growth of this species by inhibiting the acyl-CoA reductase of this invention. The enzyme of the present invention shows significant amino acid sequence similarity to two open reading frames from otherwise anonymous cDNA clones from the plant Arabidopsis thaliana (L.) and describe methods for showing the acyl CoA reductase activity of the gene products corresponding to those plant genes. The Arabidopsis genes can be used to obtain structurally similar genes from other plant species by a variety of methods that are known to those skilled in the art. In particular, the Arabidopsis genes may be used as hybridization probes to screen cDNA or genomic libraries prepared from other species. Alternately, the genes from other species may be recognized by scanning databases of partially or completely sequenced cDNA clones for clones that exhibit significant nucleotide or deduced amino acid sequence similarity. For instance genes that exhibit greater than about 60% overall nucleotide similarity and as little as about 30% deduced amino acid sequence similarity are typically considered to be genes or gene products of similar or identical function. Extensive collections of such partial sequences are already available for a number of plants species and the collections are expected to expand in the near future. In addition, the sequences of the Arabidopsis gene products may be used to design degenerate oligonucleotide primers that encode all codons capable of producing a given region of amino acid sequence. Pairs of primers can then be used to amplify a fragment of a corresponding gene from genomic DNA or cDNA of another species, and the amplified fragment may then be used as a hybridization probe form the complete gene or cDNA sequence.

SUMMARY OF THE INVENTION

It is an object of the invention to provide an acyl-CoA reductase protein which is active in the formation of a fatty aldehyde intermediate from a fatty acyl CoA substrate. No gene encoding an enzyme of this class has previously been described in the scientific literature. The sequence of the gene and polypeptide do not exhibit significant sequence homology to any other enzyme or gene of proven function. Of particular interest, although the invention is not limited thereto, is an acyl-CoA reductase protein from a bacterium, especially the bacterium A. calcoaceticus.

It is also an object of the invention to provide an amino acid sequence for an acyl-CoA reductase protein and a nucleic acid sequence which encodes such a protein. It is a particular object of the invention to provide nucleic acid and amino acid sequences for acyl-CoA reductase from the bacterium A. calcoaceticus as exemplified by SEQ ID NO:1 and SEQ ID NO:2.

The term acyl-CoA reductase protein, as used herein, is intended to mean any sequence of amino acids, including proteins, polypeptides and peptide fragments, which is active in catalyzing the reduction of acyl-CoA to the corresponding aldehyde.

Although the enzyme of this invention exhibits demonstrable in vitro activity with acyl-CoA substrates, the existence of homologous enzymes that utilize acyl-ACP substrates is envisioned because of the existence of other enzymes that utilize both acyl-CoA or acyl-ACP substrates.

An example of such an enzyme is stearoyl-ACP desaturase (Shanklin and Somerville, 1990).

A reductase of the invention may be active with a variety of acyl-CoAs, including those of different carbon chain lengths and degrees of saturation, although it may be more highly active with specific preferred substrates. In general, the reductase of the invention has activity towards at least those acyl-CoA substrates wherein the chain length of the acyl group is between 14 and 24 carbons, more preferably between 16 and 20 carbons (Dewitt et al., 1982). The substrate may be saturated or unsaturated.

A nucleic acid sequence encoding a bacterial acyl CoA reductase of the invention is considered to include genomic, cDNA and mRNA sequences. The term encoding, as used herein, is intended to mean that the sequence corresponds to a particular amino acid sequence either in a sense or anti-sense orientation. The term recombinant, as used herein, is intended to mean that the sequence contains a genetically engineered modification through manipulation via mutagenesis, cleavage with restriction enzymes, and the like. The degree of similarity or identity between two sequences can be determined by computer algorithms such as FASTA or BLAST (Altschul et al., 1990) when the sequences are known by direct comparison of the amino acid or nucleotide sequences, or where one or both are unknown, through hybridization reactions between the sequences.

Other fatty acyl reductases are obtainable from the specific exemplified sequences provided herein. Furthermore, it will be apparent that one can obtain natural and synthetic fatty acyl reductases including modified amino acid sequences and starting materials for synthetic-protein modeling from the exemplified bacterial fatty acyl reductase and from fatty acyl reductases which are obtained through the use of such exemplified sequences. Modified amino acid sequences include sequences which have been mutated, truncated, increased and the like, whether such sequences were partially or wholly synthesized. Sequences which are actually purified from bacterial preparations or are identical or encode identical proteins thereto, regardless of the method used to obtain the protein or sequence, are equally considered naturally derived.

Thus, one skilled in the art will readily recognize that antibody preparations, nucleic acid probes (DNA and RNA) and the like may be prepared and used to screen and recover "homologous" or "related" fatty acyl reductases from a variety of bacterial sources. Typically, nucleic acid probes are labeled to allow detection, preferably with radioactivity although enzymes or other methods may also be used. For immunological screening methods, antibody preparations either monoclonal or polyclonal are utilized. Polyclonal antibodies, although less specific, typically are more useful in gene isolation. For detection, the antibody is labeled using radioactivity or any one of a variety of second antibody/enzyme conjugate systems that are commercially available.

Homologous sequences are found when there is an identity of sequence and may be determined upon comparison of sequence information, nucleic acid or amino acid, or through hybridization reactions between a known fatty acyl reductase and a candidate source. Conservative changes, such as Glu/Asp, Val/Ile/Leu, Ser/Thr, Arg/Lys and Gln/Asn may also be considered in determining sequence homology. In general, these substitutions are expected to have relatively minor effects on the structure and function of a protein and are considered to be equivalent. Insertions or deletions of one or two amino acids are also considered to be neutral. Typically, a lengthy nucleic acid sequence may show as little as 50–60% sequence identity, and more preferably at least about 70% sequence identity, between the target sequence and the given bacterial fatty acyl reductase of interest excluding any deletions which may be present, and still be considered related. Amino acid sequences are considered to be evolutionarily related, and therefore of similar or identical function, when they exhibit as little as as 25% sequence identity between regions of about 100 amino acids or more(See generally, Doolittle, 1986).

A genomic or other appropriate library prepared from the candidate organism of interest may be probed with conserved sequences from the fatty acyl-CoA reductase to identify homologously related sequences. Use of an entire coding sequence or other sequence may be employed if shorter probe sequences are not identified. Positive clones are then analyzed by restriction enzyme digestion and/or sequencing. Probes can also be considerably shorter than the entire sequence. Oligonucleotides may be used, for example, but should be at least about 10, preferably at least about 15, more preferably at least 20 nucleotides in length. When shorter length regions are used for comparison, a higher degree of sequence identity is required than for longer sequences. Shorter probes are often particularly useful for polymerase chain reactions (PCR), especially when highly conserved sequences can be identified. (See, Gould, et al., PNAS USA (1989) 86:1934–1938.)

When longer nucleic acid fragments are employed (>100 bp) as probes, especially when using complete or large cDNA sequences, one would screen with low stringencies (for example 40–50° C. below the melting temperature of the probe) in order to obtain signal from the target sample with 20–50% sequence deviation.

In a preferred embodiment, a bacterial fatty acyl CoA reductase of this invention will have at least about 30% overall amino acid sequence identity, and more preferable at least about 50% overall amino acid sequence identity with the exemplified bacterial fatty acyl CoA reductase. In particular, bacterial fatty acyl CoA reductases which are obtainable from an amino acid or nucleic acid sequence of an A. calcoaceticus fatty acyl CoA reductase are especially preferred.

Sequences such as shown in SEQ ID NO:1 be used to identify homologous fatty acyl reductases, and the resulting sequences obtained therefrom may also provide a further method to obtain bacterial fatty acyl CoA reductases from other sources. In particular, PCR may be a useful technique to obtain related bacterial fatty acyl CoA reductases from sequence data provided herein. One skilled in the art will be able to design oligonucleotide probes based upon sequence comparisons or regions of typically highly conserved sequence. Of special interest are nucleic acid probes, or preferably PCR primers, based upon the sequence of amino acids from residue 20–29 and 98–106 and 125–131 and 196–204 in SEQ ID NO:2 because these regions of sequence are shown herein to be highly conserved between acyl-CoA reductases from different species of bacteria. Details relating to the design and methods for a PCR reaction using these probes is described more fully in the examples.

It should also be noted that the bacterial fatty acyl CoA reductases from a variety of sources can be used to investigate fatty acid reduction in a wide variety of bacterial and in vivo applications. Because all bacteria appear to synthesize fatty acids via a common metabolic pathway, the study and/or application of one bacterial fatty acyl CoA reductase to a heterologous bacterial host may be readily achieved in a variety of species.

Once the nucleic acid sequence is obtained, the transcription, or transcription and translation (expression), of the bacterial fatty acyl-CoA reductase in a host cell is desired to produce a ready source of the enzyme and/or modify the composition of fatty acids, alcohols, aldehydes and/or wax esters found therein. Other useful applications may be found when the host cell is a plant host cell.

For example, by increasing the amount and kind of fatty acyl CoA reductase available to a plant, the production of fatty alcohols may be achieved. When the production of such fatty alcohols takes place in plants that also contain an endogenous or introduced gene for fatty acyl-CoA:fatty alcohol acyltransferase such as that disclosed in U.S. Pat. No. 5,445,947, it is envisioned that wax esters will be synthesized.

While an acyl CoA reductase which is obtainable from *A. calcoaceticus* is especially preferred, reductases from other species such as *Mycobacterium tuberculosis* and other species of bacteria are also included. The acyl CoA reductases of the invention may have preferential activity toward longer or shorter chain fatty acyl substrates, or toward substrates with different degrees of saturation. For example, palmitoyl-CoA (16:0-CoA), stearoyl-CoA (18:0-CoA) and palmitoleoyl-CoA (16:1$^{\Delta 7}$-CoA) are substrates for the enzyme from *A. calcoaceticus*. Preferential activity of a reductase of the invention toward a particular fatty acyl substrate can be determined by comparison of rates of fatty alcohol product formation obtained with different substrates.

It is a further object of the invention to provide cells containing recombinant constructs coding for acyl-CoA reductase sequences. Cells which contain the preferred reductase from the bacterium *A. calcoaceticus*, especially as disclosed in SEQ ID NO:1 are of particular interest.

It is yet an additional object of the invention to provide host cells containing the reductase of the invention as a result of the expression of the recombinant constructs of the invention, and thereby provide a method of producing and optionally recovering the reductase of the invention from a host cell.

It will be recognized that not only the reductase of the invention, but also the products of the reductase may be produced and recovered from host cells under suitable conditions. Thus, it is a further object of the invention to provide a host cell and means of production for the products of the reductase. Such products are considered to include not only aldehydes which may be the immediate result of the activity of the reductase on acyl-CoA, but also alcohols, waxes and wax esters that may result from the further action of cellular enzymes on such aldehydes. This is considered to include enzymes which are naturally present in the host cell, or those which are introduced by genetic engineering methods. For example, the genes for wax synthases from bacteria, fungal, plant or animal sources may be used in conjunction with the genes of this invention to produce wax esters in transgenic hosts. As mentioned above, among the useful end products contemplated in this regard are wax esters. However, in addition to wax synthases that utilize only long chain fatty acyl-CoA substrates, wax synthase enzymes that utilize short chain acyl-CoAs, or other CoA species may be used to produce novel esters of the long-chain alcohols of this invention.

The term wax or wax ester, as used herein, is intended to mean the ester of a fatty acid and a long chain alcohol.

The term fatty acid, as used herein, is intended to mean an organic, acid of carbon chain length 8–34 which contains a terminal carboxyl group. With reference to the fatty acyl-CoA substrate for the acyl-CoA reductase, a fatty acid may be saturated or unsaturated, straight or branched chain. When referring to the fatty acyl-CoA substrate for wax synthase, no specific limitations are envisioned on the structure of the compound.

The term acyl, as used herein is intended to mean a fatty acid radical derived from a fatty acid by the removal of the hydroxyl group.

The term fatty alcohol, as used herein, is intended to mean an organic alcohol of carbon chain length 8–34.

The term fatty acyl substrate, as used herein, is intended to mean acyl-CoA and acyl-ACP.

The term aldehyde, as used herein, is intended to mean any aldehyde which is the product of the action of the acyl-CoA reductase of the invention on an acyl-CoA substrate.

The compositions and methods of the invention have many important scientific and industrial applications. The DNA sequence of the reductase of the invention can be used to identify similar genes from other organisms. This can be done by using the DNA (SEQ ID No 1) and protein sequence (SEQ ID No 2) as a template to search the DNA databases for other genes and proteins with similar sequences. Additionally, the protein sequence can be used to construct degenerate oligonucleotides which can be used together with PCR to isolate similar genes (Gould et al., 1989). Also, the gene itself can be labelled and used as a probe to identify other genes by low stringency Southern analysis.

Because of the gene's direct involvement in wax ester biosynthesis, it has many important industrial uses. It could be up regulated in *A. calcoaceticus* or other microbial species to overproduce wax esters for commercial production, or used to transform other organisms for fatty alcohol and fatty aldehyde production. Additionally the gene could be used in combination with a gene encoding a wax ester synthase for the synthesis of wax esters. Yeasts are candidates for wax ester production. Plants are also excellent candidates for wax ester production. Expression of the gene in seed tissues could also allow a seed to accumulate significant quantities of fatty alcohols, fatty aldehydes or wax esters. Seed could then be harvested from such transformed species and extracted for the alcohols, aldehydes or waxes, instead of oil. The wax esters produced from a transgenic species, or from *A. calcoaceticus* itself have many industrial applications, acting as substitutes for sperm whale oil and jojoba oil due to their similar chemical properties. These esters could be used as lubricants to reduce friction between mechanical parts, additionally, they could be used in steel cutting oil. Wax esters also play a very important role in the cosmetics industry where they are incorporated into creams, oils, balms, shampoos and conditioners. Other possibilities for wax esters lie in the medical community. Here, because of the inability of many organisms to utilize wax esters as a carbon source, and because of their hydrophobic nature, they can act as delivery vehicles for the transportation of medicines in the form of salves and lotions to individuals suffering from skin ailments, burns or injuries. Wax esters can also be used to coat medicinal compositions for ease of administration or to introduce more controlled release rates from tablets and capsules. Another medical use of wax esters are as a medical treatment in the form of a laxative.

Because they are not readily metabolized, wax esters might also have utility as food additives in the form of a "calorie free" fat. The liquid wax esters produced by *A. calcoaceticus* and other species could be used as a fat substitute for production of fat-free snacks and the like. Foods cooked and fried in such an ingredient would have all the properties of a food cooked in such a manner (texture and possibly taste), but without the undesired effects of calories. It might also be used in part, or as a substitute, in such products as salad dressings, making them "fat-free", or lower in fat.

The reductase gene of the invention from *A. calcoaceticus* is particularly unique in the fact that the waxes produced from *A. calcoaceticus* can be very different. For example, it has been observed that when *A. calcoaceticus* is grown in the presence of hydrocarbons of different chain lengths and saturation, those hydrocarbons are directly converted into wax esters (Dewitt et al., 1982). Although it is not known how many different acyl-CoA reductases are present in this species, the implication is that if only one enzyme is present it is capable of accepting fatty acyl-CoA substrates of different chain lengths. This is in contrast to observations in other species. For example, in jojoba and sperm whales, wax esters are of a particular size and saturation, suggesting that the enzymes from these species may be highly substrate specific. This allows for "custom" wax ester production in *A. calcoaceticus* where one could vary the carbon sources in the growth medium, thus giving rise to unique wax esters that vary in carbon length and saturation. In this manner a mixture of wax esters can be produced with different fatty acid and fatty alcohol segments depending on what is included in the culture medium. Conversely, it will also be possible to produce specifically sized wax esters with a known degree of saturation. Because of the lack of substrate specificity, in vivo or in vitro synthesis of "custom made" wax esters having unique substrates that branch off the alkoxy and acyl segments of the wax esters is possible. This will allow for new kinds of polymers of waxes, or waxes with active side chains that could be used in other industrial applications or in medicine.

A nucleic acid sequence encoding an acyl-CoA reductase of this invention may include genomic, cDNA or mRNA sequence. By "encoding" is meant that the sequence corresponds to a particular amino acid sequence either in a sense or anti-sense orientation. By "recombinant" is meant that the sequence contains a genetically engineered modification through manipulation via mutagenesis, restriction enzymes, and the like. A gene sequence may or may not contain pre-processing sequences.

Once the desired acyl-CoA reductase nucleic acid sequence is obtained, it may be manipulated in a variety of ways. Where the sequence involves non-coding flanking regions, the flanking regions may be subjected to resection, mutagenesis, etc. Thus, transitions, transversions, deletions, and insertions may be performed on the naturally occurring sequence. In addition, all or part of the sequence may be synthesized. In the structural gene, one or more codons may be modified to provide for a modified amino acid sequence, or one or more codon mutations may be introduced to provide for a convenient restriction site or other purpose involved with construction or expression. The structural gene may be further modified by employing synthetic adapters, linkers to introduce one or more convenient restriction sites, or the like.

The nucleic acid or amino acid sequences encoding an acyl-CoA reductase of this invention may be combined with other non-native, or "heterologous", sequences in a variety of ways. By "heterologous" sequences is meant any sequence which is not naturally found joined to the acyl-CoA reductase, including, for example, combination of nucleic acid sequences from the same organism which are not naturally found joined together.

Potential host cells include both prokaryotic and eukaryotic cells. A host cell may be unicellular or found in a multicellar differentiated or undifferentiated organism depending upon the intended use. Cells of this invention may be distinguished by having an acyl-CoA reductase foreign to the wild-type cell present therein, for example, by having a recombinant nucleic acid construct encoding an acyl-CoA reductase therein.

Depending upon the host, the regulatory regions will vary, including regions from viral, plasmid or chromosomal genes, or the like. For expression in prokaryotic or eukaryotic microorganisms, particularly unicellular hosts, a wide variety of constitutive or regulatable promoters may be employed. Expression in a microorganism can provide a ready source of the enzyme. Among transcriptional initiation regions which have been described are regions from bacterial and yeast hosts, such as *E. coli, B. subtilis, Saccharomyces cerevisiae,* including genes such as beta-galactosidase, T7 polymerase, tryptophan E and the like.

In some instances, the constructs will involve regulatory regions functional in plants which provide for modified production of an acyl-CoA reductase, and possibly, modification of the fatty acid composition. The open reading frame, coding for the acyl-CoA reductase or functional fragment thereof will be joined at its 5' end to a transcription initiation regulatory region such as the wild-type sequence naturally found 5' upstream to a highly expressed plant structural gene. Numerous plant transcription initiation regions are available which provide for transcription of the structural gene functions in a wide variety of cell and tissue types. Among transcriptional initiation regions used for plants are such regions associated with the structural genes such as the promoters for nopaline and mannopine synthases, or with the napin promoter, the cauliflower mosaic virus 35S promoters and the like. The transcription/translation initiation regions corresponding to such structural genes are found immediately 5' upstream to the respective start codons. In embodiments wherein the expression of the acyl-CoA reductase protein is desired in a plant host, the use of part of the complete acyl-CoA reductase gene is desired; namely the structural gene sequence may be employed. In general a different promoter is desired, such as a promoter native to the plant host of interest or a modified promoter, i.e., having transcription initiation regions derived from one gene source and translation initiation regions derived from a different gene source, including the sequence encoding the acyl-CoA reductase of interest, or enhanced promoters, such as double 35S CaMV promoters, the sequences may be joined together using standard techniques.

For such applications when 5' upstream non-coding regions are obtained from other genes regulated during seed maturation, those preferentially expressed in plant embryo tissue, such as napin-derived transcription initiation control regions, are desired. The properties and uses of such seed-specific promoters are summarized in a review by M. Bevan, V. Colot, K. M. Hammond et al. (1993) Transcriptional control of plant storage protein genes. Phil. Trans. Roy. Soc. Lond. Biol. Sci. 342,209–215. Such 'seed-specific promoters' may be obtained and used in accordance with the teachings of U.S. Pat. No. 5,420,034, issued May 30, 1995, entitled "Seed-specific Transcriptional Regulation", and U.S. Pat. No. 5,530,194 issued Jun. 25, 1996 entitled "Sequences Preferentially Expressed In Early Seed Development and Methods Related Thereto," which patents are hereby incorporated by reference.

Transcription initiation regions which are preferentially expressed in seed tissue, i.e., which are undetectable in other plant parts, are considered desirable for fatty acid modifications in order to minimize any disruptive or adverse effects of the gene product.

Regulatory transcript termination regions may be provided in DNA constructs of this invention as well. Transcript termination regions may be provided by the DNA sequence encoding the fatty acyl reductase or a convenient transcription termination region derived from a different gene source, for example, the transcript termination region which is naturally associated with the nopaline synthase gene from *Agrobacterium tumefaciens.* Where the transcript termination region is from a different gene source, it will contain at least about 0.5 kb, preferably about 1–3 kb of sequence 3' to the structural gene from which the termination region is derived.

Plant expression or transcription constructs having an acyl-CoA reductase as the DNA sequence of interest for increased or decreased expression thereof may be employed with a wide variety of plant life, particularly, plant life involved in the production of vegetable oils for edible and industrial uses. Most especially preferred are temperate oilseed crops. Plants of interest include, but are not limited to rapeseed (Canola and high erucic acid varieties), sunflower, safflower, cotton, Cuphea, soybean, peanut, coconut, *Brassica juncea,* crambe, oil palms and corn. Depending on the method for introducing the recombinant constructs into the host cell, other DNA sequences may be required. Importantly, this invention is applicable to dicotyledonous and monocotyledons species alike and will be readily applicable to new and/or improved transformation and regulation techniques.

The method of transformation is not critical to the instant invention; various methods of plant transformation are currently available. As newer methods are available to transform crops, they may be directly applied hereunder. For example, many plant species naturally susceptible to Agrobacterium infection may be successfully transformed via tripartite or binary vector methods of Agrobacterium mediated transformation. In addition, techniques of microinjection, DNA particle bombardment, electroporation have been developed which allow for the transformation of various monocot and dicot plant species.

In developing the DNA construct, the various components of the construct or fragments thereof will normally be inserted into a convenient cloning vector which is capable of replication in a bacterial host, e.g., *E. coli.* Numerous vectors exist that have been described in the literature. After each cloning, the plasmid may be isolated and subjected to further manipulation, such as restriction, insertion of new fragments, ligation, deletion, insertion, resection, etc., so as to tailor the components of the desired sequence. Once the construct has been completed, it may then be transferred to an appropriate vector for further manipulation in accordance with the manner of transformation of the host cell.

Normally, included with the DNA construct will be a structural gene having the necessary regulatory regions for expression in a host and providing for selection of transformant cells. The gene may provide for resistance to a cytotoxic agent, e.g., antibiotic, heavy metal, toxin, etc., complementation providing prototrophy to an auxotrophic host, viral immunity or the like. Depending upon the number of different host species into which the expression construct or components thereof are introduced, one or more markers may be employed, where different conditions for selection are used for the different hosts.

It is noted that the degeneracy of the DNA code provides that some codon substitutions are permissible of DNA sequences without any corresponding modification of the amino acid sequence.

As mentioned above, the manner in which the DNA construct is introduced into the plant host is not critical to this invention. Any method which provides for efficient transformation may be employed. Various methods for. plant cell transformation include the use of Ti- or Ri-plasmids, microinjection, electroporation, DNA particle bombardment, liposome fusion, DNA bombardment or the like. In many instances, it will be desirable to have the construct bordered on one or both sides of T-DNA, particularly having the left and right borders, more particularly the right border. This is particularly useful when the construct uses *A. tumefaciens* or *A. rhizogenes* as a mode for transformation, although the T-DNA borders may find use with other modes of transformation.

Where Agrobacterium is used for plant cell transformation, a vector may be used which may be introduced into the Agrobacterium host for homologous recombination with T-DNA or the Ti- or Ri-plasmid present in the Agrobacterium host. The Ti- or Ri-plasmid containing the T-DNA for recombination may be armed (capable of causing gall formation) or disarmed (incapable of causing gall), the latter being permissible, so long as the vir genes are present in the transformed Agrobacterium host. The armed plasmid can give a mixture of normal plant cells and gall.

In some instances where Agrobacterium is used as the vehicle for transforming plant cells, the expression construct bordered by the T-DNA border(s) will be inserted into a broad host spectrum vector, there being many appropriate derivatives of broad host spectrum vectors described in the literature. (See, for example, K. Lindsey (1996) Plant Transformation systems. In *Transgenic Plants: A production System for Industrial and Pharmaceutical Proteins*, MRL Owen and J pen, eds., John Wiley & Sons Ltd, NY pp 1–25). Included with the expression construct and the T-DNA will be one or more markers, which allow for selection of transformed Agrobacterium and transformed plant cells. A number of markers have been developed for use with plant cells, such as resistance to kanamycin, the aminoglycoside G418, hygromycin, or the like. The particular marker employed is not essential to this invention, the preferred marker in a given situation depending on the particular host and the manner of construction.

For transformation of plant cells using Agrobacterium, explants may be combined and incubated with the transformed Agrobacterium for sufficient time for transformation to occur, the bacteria killed, and the plant cells cultured in an appropriate selective medium. Once callus forms, shoot formation can be encouraged by employing the appropriate plant hormones in accordance with known methods and the shoots transferred to rooting medium for regeneration of plants. The plants may then be grown to seed and the seed used to establish repetitive generations and for isolation of vegetable oils.

The invention now being generally described, it will be more readily understood by reference to the following examples which are included for purposes of illustration only and are not intended to limit the present invention.

BRIEF DESCRIPTION OF THE DRAWINGS

FIG. 3 Alignment of the deduced amino acid sequence of a fatty acyl-CoA reductase with the corresponding gene from *A. calcoaceticus*, and the locations of an EcoRV restriction site and regions of sequences homologous to oligonucleotide primers used in manipulations of the nucleic acid sequence.

FIG. 5 FASTA alignment of regions of amino acid sequence of the *A. calcoaceticus* acrl gene product with ORF2 from GenBank accession number U27357 encoding a polypeptide of unknown function from *Mycobacterium tuberculosis*.

FIG. 7 FASTA alignment of a region of *A. calcoaceticus* acrl gene product with an open reading frame on an anonymous partial cDNA sequence from *Arabidopsis thaliana* (GenBank accession number T21872). and Z27263

FIG. 8 FASTA alignment of a region of *A. calcoaceticus* acrl gene product with an an open reading frame on anonymous partial cDNA sequence from *Arabidopsis thaliana* (GenBank accession number Z27263).

DETAILED DESCRIPTION OF THE INVENTION

EXAMPLE 1

Figure 1:
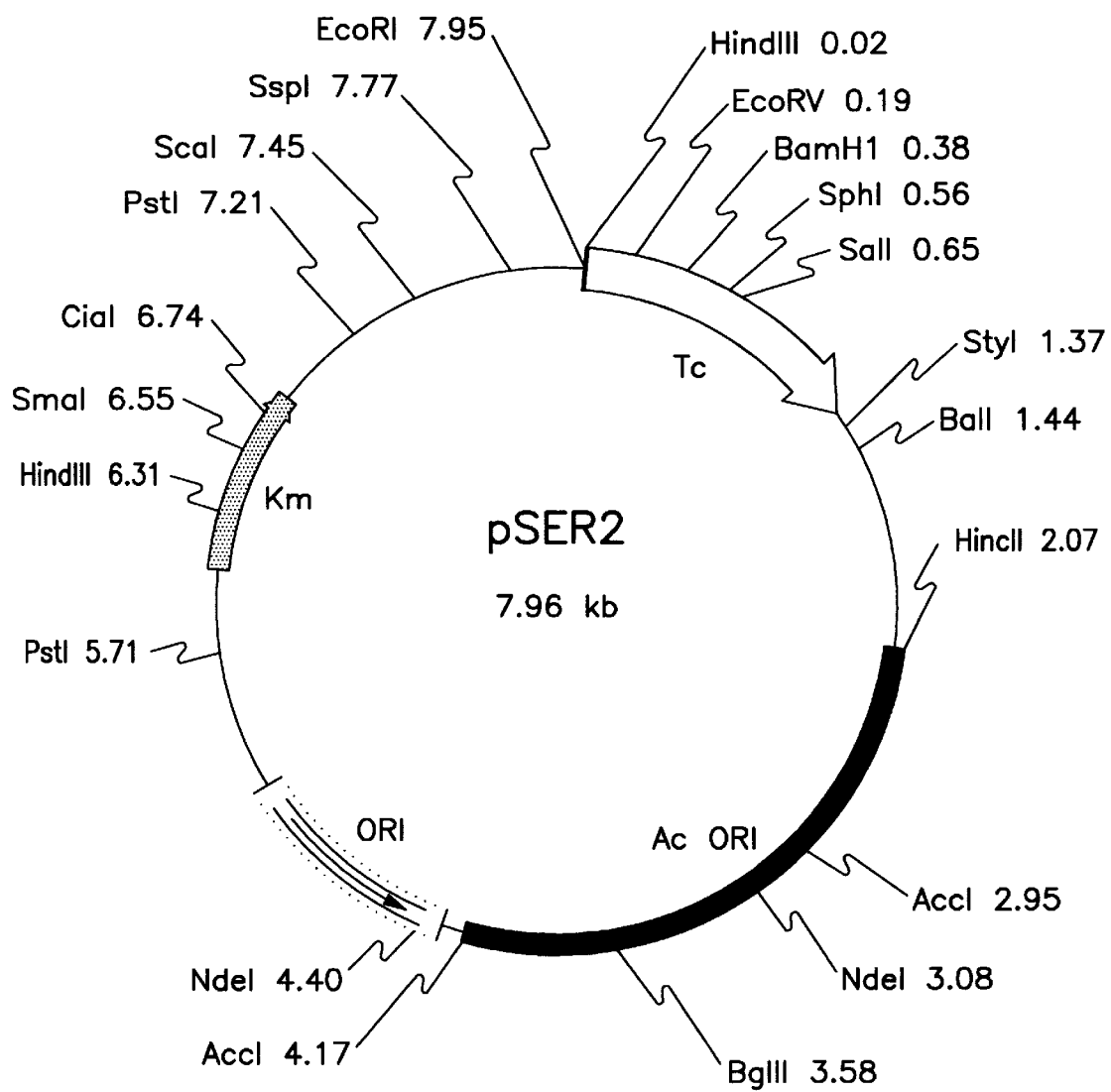
FIG. 1 The structure of plasmid pSER2.

Isolation of Mutants of Acinetobacter Deficient in Wax Ester Accumulation

Typically when *A. calcoaceticus* is grown under nutrient starvation conditions it accumulates wax esters internally as a means of carbon storage. A mutant of *A. calcoaceticus* strain BD413, designated wow5, was identified, which failed to accumulate wax esters when grown under wax inducing (nitrogen starvation) conditions.

Growth of Bacteria

The *A. calcoaceticus* strains used in the procedures described here are all derived from ATCC#33305 (also known as strain BD413).

Low nitrogen minimal medium (per liter, 2.0 g $KH_2PO_4$, 1.18 g succinic acid, 0.1 g $NH_4SO_4$, pH adjusted to 7.0 with solid KOH, after autoclaving add 20 ml of sterilized 2% $MgSO_4$) was used in experiments with *A. calcoaceticus* strain BD413 to induce wax ester formation. High nitrogen minimal medium was the same as the above except that it also contained 1.0 g $NH_4SO_4$ per liter. For other purposes such as DNA isolation, *A. calcoaceticus* was grown and maintained on LB medium (10 g bactotryptone, 5 g bacto-yeast extract and 10 g NaCl per liter, pH 7.0). For chemical feeding experiments in which compounds such as hexadecane, hexadecanol and cis-11-hexadecenal were provided as carbon sources, the above minimal media were used with the addition of 0.3% of the substrate. Hexadecane and hexadecanol were sonicated for approximately 2 minutes in the media to generate a suspension. *A. calcoaceticus* cultures were typically grown overnight at 30° C. In the case of larger volume cultures(i.e. 50 mls and larger), 3 ml overnight cultures were collected by centrifugation, the cell pellet was washed in new media, recentrifuged and then added to the fresh media, before being incubated at 30° C. overnight. Maintenance and growth of *Escherichia coli* stains was on LB with appropriate antibiotics. Antibiotics were used in the following concentrations: Ampicillin 100 µg/ml, Chloramphenicol 50 µg/ml, Kanamycin 25 µg/ml, Rifampicin 50 µg/ml and Tetracycline 15 µg/ml.

Isolation of Mutants

In order to isolate mutants deficient in wax ester accumulation, a 22 ml culture of *A. calcoaceticus* strain BD413 was grown in LB broth at 30° C. until the observed optical density at 600 nm was approximately 0.6. At this point, 2.3 mg of nitrosoguanidine (NTG) (0.1 mg/ml final concentration) was added and the culture was allowed to incubate for an additional 50 minutes at room temperature with shaking. At 30 and 50 minutes a 3 ml sample was removed, washed twice with LB broth and incubated at 30° C. overnight. The next day, samples were spread onto LB plates and the resulting colonies were transferred onto LB master plates in arrays of 100 colonies per 100 mm petri plate. This master plate was replica plated onto a minimal media plate with low nitrogen to induce wax ester accumulation. Following growth of the colonies (approximately 24 h at 30° C.) the colonies were then stained by irrigating the plates with sudan black B (0.02% in 50:45:5 dimethylsulfoxide (DMSO):ethanol:water) and gently shaken for approximately 20 minutes. The stain was aspirated away and the plates were carefully washed with 70% ethanol and gently shaking for approximately 2 minutes. Lighter staining colonies were identified from the stained plates and the corresponding colony from the master plate was subsequently analyzed by thin layer chromatography (TLC) as described below. Because wax esters are very nonpolar, colonies containing these compounds are darker in color, after being stained with Sudan black B, than colonies lacking neutral lipid accumulation. Following such a procedure approximately 10% of the mutagenized colonies were selected as "lighter staining". To determine if these colonies were truly affected in wax ester accumulation, the colonies from the master plate were restreaked and then cultured in low nitrogen media for analysis by TLC.

*A. calcoaceticus* samples to be analyzed by TLC were typically grown in 3 ml cultures in low nitrogen minimal media. Samples were collected by centrifugation (5 minutes at 3000×g) and the medium removed. Pellets were washed in additional medium, centrifuged, and the supernatant removed. Neutral lipids were isolated by extracting the cells with 75 µl chloroform:methanol (50:50) followed by phase separation using 25 µl 1.0 M potassium chloride in 0.2 M phosphoric acid. Samples were centrifuged at 2000×g in a clinical centrifuge at room temperature for 2 minutes. The chloroform phase was then directly spotted onto 19 channel Si-250 TLC plates containing preadsorbant layers (Baker) that had been charged by incubating at 120° C. for 10 minutes. Ten µl of 2 mg/ml standards of known lipid species were also loaded for comparison during subsequent analysis. Lipids were resolved by developing the plates in hexane:ethyl ether:acetic acid (90:10:1). Samples were visualized by spraying the plates with 50% sulfuric acid and charring at 160° for approximately 5 minutes, or by immersing the plate in iodine vapor until visualization of the lipids was possible.

A total of approximately 6400 mutagenized colonies were screened using these procedures. A total of 25 mutants were recovered, which were divided into 3 phenotypic classes. Class I mutants lacked wax but had normal levels of other neutral lipids (wax$^-$tag$^+$), class II mutants had wax but lacked other neutral lipids (wax$^+$tag$^-$) and class III mutants lacked both wax and neutral lipids (wax$^-$tag$^-$). All mutants were assigned the symbol wow, for without wax. The wow15 mutant, which had no apparent growth defect and lacked wax esters but had essentially normal levels of triacylglycerols, was chosen for all further studies.

Based on previous observations by other researchers it was known that *A. calcoaceticus* could be cultured in the presence of alkanes and fatty alcohols as a carbon source (Dewitt et al., 1982). These previous studies also showed that when *A. calcoaceticus* is incubated in the presence of these substrates they are directly utilized in wax ester accumulation. Similar analyses of the wow15 mutant was carried out in order to characterize the sites of the biochemical lesions in this mutant.

Culturing the wow15 mutant in the presence of hexadecanol (a 16 carbon alcohol) as a substrate showed that the wow15 mutant was able to synthesize wax esters. This implies that, since wax biosynthesis from hexadecanol is still possible in this mutant, the acyl-CoA (or acyl-ACP) fatty alcohol transferase was not affected. Thus, the fact that the wow15 mutant did not accumulate wax when grown on hexadecane suggests that it was deficient in one or both of the two reductase steps thought to be required for the synthesis of fatty alcohols from fatty acyl-CoAs.

An additional feeding experiment was carried out in which the wow15 mutant was grown in the presence of a 16 carbon aldehyde (cis-11-hexadecenal) as described above. When this was done the mutant was able to synthesize wax esters. These results established that the mutant was defective in conversion of the acyl-CoA or acyl-ACP to the corresponding aldehyde.

EXAMPLE 2

Isolation of a Gene that Complements the Wow15 Mutation

Construction of Vector pSER2

In order to obtain expression of any cloned bacterial gene in *A. calcoaceticus*, we constructed several new plasmid vectors for the purpose. An *A. calcoaceticus*/*E. coli* shuttle vector, pWH1274, had already been constructed and described by Hunger et al. (1990). It is a pBR322 derivative containing ampicillin and tetracycline resistance markers and an *A. calcoaceticus* origin of replication in addition to the origin of replication from *E. coli*. One problem with this vector is that *A. calcoaceticus* is naturally resistant to ampicillin, making selection with that particular marker difficult in this species. Therefore, pWH1274 was modified by inserting a kanamycin resistance marker taken as a PstI fragment from pUC4% into the PstI site of the ampicillin cassette of pWH1274, thus inactivating it. The resulting plasmid containing the kanamycin cassette was called pSER2 (FIG. 1).

TABLE 1

Bacterial strains

| Bacterial Strains | Relevant Characteristics | Source or Reference |
|---|---|---|
| *A. calcoaceticus* | | |
| BD413 | wild type strain of *A. calcoaceticus* | ATCC #33305 |
| wow15 | wax-deficient mutant of BD413 | mutagenesis |
| wow15:Rif | Rifampicin resistant mutant of wow15 | spontaneous |
| *E. coli* | | |
| HB101 | F'proA2 recA13 mcrB | |
| DH5α | F'/endA1 recA1 Δ(lacZYA-argF) U169 (φ80dlacΔ(lacZM15) | Gibco BRL |
| MM294 | F-endA1 hsdR17 thi-1 | |
| BD21 (DE3) | F-ompT hsdS$_B$(r$_B^-$m$_B^-$) gal dcm(DE3) | Novogen |
| MG1655 | wild type, for carrying out Tn10 mutagenesis | Kleckner et al., 1991 |
| Phage | | |
| λNK1324 | mini-Tn10Cam | Kleckner et al. 1991 |

TABLE 2

Plasmid sources and derivation.

| Plasmid | Description or Construction | Source or Reference |
|---|---|---|
| pBS | Bluescript Vector KS+ | Stratagene |
| pRK2013 | Km self-transmissible RK2 derivative containing CO1E1 replicon and transfer functions to mobilize RK2 derivatives | |
| pLA2917 | Cosmid Vector (Tet') derived from RK2 | |
| pET21 | Expression vector for *E. coli*. | Novagen |
| pSER2 | *A. calcoaceticus/E. coli* shuttle vector (Tet'Km') | Figure 1 |
| pSR2 | Bluescript with EcoRV fragment from 4A-55 | |
| pSR6 | Bluescript with EcoRV fragment from 4A-55 | |
| pSER2:acr1 | pSER2 derivative containing PCR fragment amplified using primers P5 and P6 | |
| pET21:acr1 | pET21 derivative for protein expression of acr1 in *E. coli* BL21(DE3). Contains PCR fragment amplified using primers P7 and P8 | |
| 4A-55 | pLA2917 derived cosmid clone complementing the wow15 mutant | |
| 2A-87 | pLA2917 derived cosmid clone complementing the wow15 mutant | |

General Methods

Genomic DNA for Southern blot analysis was prepared by growing 3 ml cultures of the bacteria overnight in LB at 30° C. Half of the culture was collected by centrifugation in a microfuge at maximum speed for 5 minutes. The pellet was washed with 500 μl of 10 mM Tris-HCl (pH 7.6)+5 mM EDTA (pH 8.0). The sample was centrifuged, and resuspended in 350 μl of the above buffer. To this 50 μl of 10% SDS and 100 μl of 2.5 mg/ml stock of pronase (Sigma) was added. The samples were incubated at 37° C. for 1 hour. Samples were then drawn through a 1 ml syringe with an attached 18 gauge needle 3 times to shear the DNA. Samples were extracted once in 1 volume of phenol, twice in 1 volume of phenol/chloroform (50:50) and once in 1 volume of chloroform. The supernatant was removed and the DNA precipitated from solution by the addition of 2 volumes of 100% ethanol. DNA was recovered by spindling it out of solution with a capillary tube that had been sealed and bent using a bunsen burner. As much ethanol was removed as possible by gently touching the sample to the side of the eppendorf tube and letting the ethanol drain off. DNA was gently transferred to 100 μl of the above buffer and allowed to enter solution by incubating the sample overnight at 4° C.

Colony lifts were prepared using ninety five millimeter nitrocellulose filters (Amersham) which were placed on top of LB plates containing 15 μg/ml of tetracycline. Replicas of the genomic library were stamped onto the filters using a sterile prong device that matched the 96 well array containing the library. The colonies on the filters were allowed to grow for approximately 6 hours at 37° C., or until colonies were just evident. Filters were removed and placed onto 3 mm Whatman paper saturated with 0.5 M NaOH, 1.5 M NaCl for 5 minutes. Next, the filters were neutralized on 3 mm Whatman paper soaked in 1 M Tris-HCL, pH 8.0 plus 1.5 M NaCl for 3 minutes. Filters were briefly washed in 2× SSC and then dried on 3 mm Whatman paper before being baked at 80° C. for 30 minutes to fix the DNA to the filter.

Restriction digestions were carried out under the conditions recommended by the manufacturer (Pharmacia). Southern blot analysis and detection was performed by standard methods. In brief, a probe is labelled by incorporation of digoxigenin-11-UTP. In detecting the probe, the filter is washed twice in 2× SSC+0.5% SDS at room temperature. Two high stringency washes were carried out at 65° C. for 15 minutes in 0.5× SSC+0.5% SDS. Finally, to detect the probe, the filter is incubated in the presence of anti-digoxigenin antibody conjugated to alkaline phosphatase (Boehringer-Mannheim). The conjugated antibody was then visualized by incubation in either Lumi-Phos 530 or nitroblue tetrazolium.

To determine if identified DNA sequences shared any similarity to previously characterized proteins, DNA sequences were typically compared by BLASTX alignment to GeneBank release 92.0 via an electronic mail server.

Isolation of a Complementing Cosmid

In order to complement the mutant phenotypes, a cosmid genomic library was prepared. *A. calcoaceticus* genomic DNA for the construction of the cosmid library was prepared in the following manner. A 200 ml culture of *A. calcoaceticus* strain BD413 was grown overnight. Cells were collected by centrifugation and resuspended in 16 mls of buffer (8% sucrose, 50 mM Tris pH 8.0, 50 mM EDTA pH 8.0). Lysozyme (Sigma) was added to a final concentration 2 mg/ml. Cells were incubated at 30° C. for 30 minutes to make spheroplasts. Twenty four milliliters of the lysis buffer (3% SDS, 0.5 M Tris pH 8.0, 0.2 M EDTA pH 8.0) was added and the sample was incubated at 65° C. for 30 minutes. The sample was then cooled on ice. A sucrose step gradient was prepared for centrifugation in the following manner. Five milliliters of 50% sucrose on the bottom, 10 mls of 20% sucrose in the middle, and 10 mls of 15% sucrose on top in the lysis buffer described above. Ten milliliters of the sample was then layered on top of the sucrose solutions and the gradient was centrifuged in an SW222 (Beckman) swing out rotor at 27,000 rpm for 3 hours at 15° C. The DNA was recovered as a pellet above the 50% sucrose step, from where it was removed to a dialysis bag. The DNA was dialyzed in 1.5 L of 1×TE (10 mM Tris-Cl, 0.1 mM EDTA) overnight, with one change of the solution. The DNA was then gently extracted with 1 volume of phenol for 10 minutes, inverting the sample every couple of minutes. Next the DNA was extracted with 1 volume of chloroform/isoamyl alcohol for 10 minutes, again inverting the sample every couple of minutes. The DNA was again removed to a dialysis bag and dialyzed in 4 L of TE for 2 days. The DNA was partially digested with SauIIIA to a mean size of approximately 25 Kb. Fragments of approximately 25 Kb and larger were size selected by running the partially digested DNA on a 0.6% agarose gel, cutting the band containing the fragments of interest from the gel, and isolating the DNA away from the agarose by electroelution using standard DNA procedures (Maniatis et al. 1982). The fragments were ligated directly to BglII-digested cosmid, pLA2917, and packaged using Gigapack Gold packaging extracts (Stratagene). Examination of the library by restriction analysis indicated that 68% of the transfectants contained inserts. Approximately 1400 colonies were transferred to LB broth in 96 well plates.

Identification of a complementary cosmid was carried out by triparental filter matings of the cosmid genomic library to a rifampicin resistant derivative of strain wow15 in the presence of MM294, a helper strain. The mutant strain wow15:Rif$^r$ was obtained by plating approximately $10^7$ unmutagenized cells of wow15 on rifampicin plates and retaining a spontaneous Rif$^r$ colony. The neutral lipids of the Rifr strain were examined by TLC to ensure that there was no significant difference from the original wow15 mutant. The cosmid library was contained in *E. coli* strain HB101 and was Tet$^r$ due to the presence of the cosmid. MM294 is a strain containing pRK2013, a helper plasmid that enables triparental mating through its mob genes. The pRK2013 plasmid imparts Km$^r$. At the end of the mating, wow15:Rif$^r$ mutants containing the cosmids can be selected by plating the product of the cross onto LB medium containing rifampicin, to select for wow15:Rif$^r$, and tetracycline to select for the presence of the cosmid. MM294 and the HB101 donor will fail to grow because they are not resistant. The wow15 strain and MM294 were grown overnight as 3 ml cultures, and the library was grown in 96 well titer plates as replicates of the original. The day of the mating, 0.5 ml of MM294 was used to inoculate a 50 ml of culture, and 3 ml of wow15 was used to inoculate a 50 ml culture. Cultures were collected at an $OD_{600}=0.6$, washed and then resuspended in 50 ml of LB. Twenty five milliters of MM294 was combined with 50 ml of the wow15 strain. Ten milliters of this mixture was drawn through a sterilized 45μ filter (85 mm in diameter) via a vacuum apparatus creating an even lawn of bacteria. The filter was then removed and placed on to an LB plate. Using sterilized set of prongs arranged to match 48 wells of the 96 well titer plates containing the library, the library was stamped onto the lawn of bacteria and matings were allowed to incubate at 30° C. overnight. Filters were then transferred to selective media containing rifampicin (50 μg/ml) and tetracycline (15 μg/ml) to select for wow15:Rif$^r$ containing the cosmids. The resulting exconjugants were then restreaked onto a master plate containing the selective medium, before being replica plated onto minimal, low nitrogen, wax inducing medium for subsequent analysis by lipophilic staining and TLC.

The lipophilic dye Sudan black B was used to identify darker staining colonies, which might contain greater amounts of neutral lipids than the mutants. These darker staining colonies were then further investigated by TLC analysis to confirm whether or not they contained normal levels of wax esters. After searching through 350 exconjugates two cosmids, 2A-87 and 4A-55, were found to complement the wow15 phenotype.

Transposon Mutagenesis of Complementary Cosmid

Because of the cosmids large size (ca. 55 Kb), the genes were localized on the cosmid by mutagenesis with transposon Tn-10. The mutagenized cosmid was then screened for insertions that eliminated the ability of the cosmid to complement the mutant phenotype.

Phage vehicle λNK1324, carrying a Tn-10 derivative which carries a gene for chlorampenicol resistance, was used to transfect *E. coli* strain MG1655 containing the cosmid 4A-55 that complemented the wow15 phenotype. Protocols for transfection, growth and maintenance of λNK1324 have been published by Kleckner et. al. (1991). Resulting colonies were selected on tetracycline (15 μg/ml) for the presence of the cosmid and chloramphenicol (50 μg/ml) for the presence of the transposon. To separate insertion events that were located in the genome versus the desired insertions in the cosmid, approximately 3000 transfectants were pooled and cosmid DNA was isolated. The resulting cosmids were used to transform E. coli strain DH5α. Cosmids with transposon insertions were selected by plating the transformants on medium containing tetracycline and chloramphenicol. One hundred and ninety two of the resulting transformants were transferred to 96-well plates and used for triparental matings with wow15 as previously described. The resulting exconjugates were then screened by TLC looking for insertions that resulted in the loss of the ability of the cosmid to complement the mutant phenotypes.

Mutagenesis of 4A-55 with a Tn-10 derived transposon, produced a total of 10 insertions out of a total of 192 that resulted in the loss of the ability of the cosmid to complement the wow15 phenotype. Two of the 10 mutations resulted in some sort of deletion or rearrangement in the cosmids that were evident when they were analyzed by restriction analysis. This left 8 insertions of interest. The approximate location of the insertions relative to the restriction map have been highlighted in FIG. 2 for the cosmid 4A-55.

Delineation of the transposons on the map was possible by using extended PCR in coordination with primers that were specific for the transposon that faced out toward primers that were specific for the region surrounding the BglII site of pLA2917.

Figure 2:
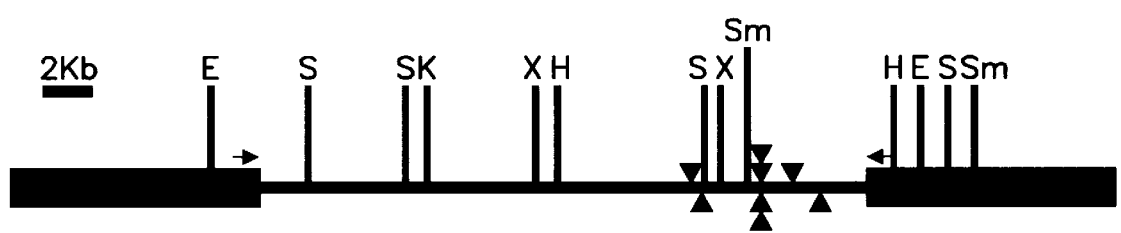
FIG. 2 Approximate location of Tn-10 insertions in cosmid 4A-55 that inactivate the acyl CoA reductase gene that complements the wow15 mutation of *A. calcoaceticus*. The insert DNA is represented by the narrow horizontal line. The cosmid vector is represented by the heavy horizontal line. The arrows facing the insert represent the position and orientation of oligonucleotide primers P1 and P2. The vertically oriented arrowheads represent the locations of Tn-10 insertions that inactivate the acrl gene. Symbols: E, EcoRI, H, HpaI, K, KpnI, S, SalI, Sm, SmaI, X, XhoI.

Primers P1 and P2 (Table 3) were designed to prime PCR extending from either side of the BglII site of pLA2917 facing in toward the insert. Additionally, primers P3 and P4 (Table 3), which are homologous to the ends of the Tn-10 element, were constructed to prime PCR that extend out, toward the edge of the insert DNA. Using one anchor on the cosmid in conjunction with the primers specific to the transposon (Table 3), it was possible to amplify the DNA in between the primers allowing us to assign a distance of the transposon relative to the anchoring (cosmid specific) primer (FIG. 2).

Transposon mapping of the cosmids was carried out using Boehringer Mannheim's Expand Long Template PCR System. Reactions contained 350 µM of dNTP's, 300 nM of each primer, 5 µl of 10× buffer 1 (17.5 mM MgCl$_2$, 500 mM Tris-HCl, pH 9.2, 160 mM (NH$_4$)$_2$SO$_4$), 0.15 µg of template DNA and 0.75 µl of the supplied enzyme mix in a total volume of 50 µl. Cycling was carried out in the following manner:

Step 1: 94° C. for 2 minutes
Step 2: 94° C. for 10 seconds
Step 3: 65° C. for 30 seconds
Step 4: 68° C. for 7 minutes
Step 5: repeat from step 2 10 more times
Step 6: 94° C. for 10 seconds
Step 7: 65° C. for 30 seconds
Step 8: 68° C. for 7 minutes +20 seconds each cylcle
Step 9: repeat from step 6 15 more times
Step 10: 68° C. for 7 minutes
Step 11: Hold at 4° C.

The localization of all of the insertions to a small region of the cosmid's DNA indicated that the gene of interest probably did not reside within an operon, or it was near the beginning of an operon. Localization of the transposons on the restriction map pointed out that there was no single restriction fragment of practical size that would encompass the region containing all of the transposon insertions.

Delineation of the Complementary Region from Cosmid 4A-55

In order to subclone a fragment containing all of the transposon insertions, the insertional mutants of cosmid 4A-55 were digested with several different enzymes (EcoRV, ClaI, and NheI) and the restriction pattern compared to that of the wild type cosmid. Digestions with EcoRV resulted in the appearance of a band in the transposon mutagenized cosmids, that was not present in the wild type cosmid, 4A-55. It was observed that the fragment that shifted did not disappear from the mutagenized lines, indicating that there were two or more EcoRV fragments of approximately the same size.

TABLE 3

Synthetic oligonucleotides used

| Primer | Sequence (5'-3') | Description |
| --- | --- | --- |
| SEQ ID NO:3 | CTTTCTTGCCGCCAAGGATCTGATG | Used in mapping the location of Tn insertions in 4A-55. Specific to 5' side of BglII site of pLA2917 in the Km cassette which originated from Tn-5. Faces toward BglII site |
| SEQ ID NO:4 | GGCCGGAGAACCTGCGTGCAAT | Same as 5' Km Tn-5 but specific to the 3' side of the BglII site. |
| SEQ ID NO:5 | GACGGGGTGGTGCGTAACGGC | Used in mapping the location of Tn insertions in 4A-55. Specific to 5' end of mini-Tn10Cm facing out. |
| SEQ ID NO:6 | CAGGCTCTCCCCGTGGAGGTAAT | Same as 5' Cm Tn-10, but specific to 3' end of the transposon. |
| SEQ ID NO:7 | GCAGGATCCTTGGGATTGAACATATTG | Used with P6 to amplify PCR product to generate pSER2:acr1. Contains BamHI linker at 5' end. |
| SEQ ID NO:8 | GCAGGATCCGGTGCGATTTATGATGTA | Used with P5 to amplify PCR product to generate pSER2:acr1. Contains BamH linker at 5' end |
| SEQ ID NO:9 | GCAGGATCCAAAACATTGGTAATTTCAGATACT | Used with P8 to amplify PCR product to generate PET21:acr1. Contains BamHI linker at 5' end. |
| SEQ ID NO:10 | GCAGAATTCGGTGCGATTTATGATGTA | Used with P7 to amplify PCR product to generate pET21:acr1. Contains EcoRI linker at 5' end |

DNA from cosmid 4A-55was digested with EcoRV, resolved on a gel, and the region of the gel containing three tightly spaced bands of approximately 4.0 kb was electroeluted. The resulting DNA was ligated to EcoRV digested pBS and transformed into E. coli strain DH5α. Colonies were screened for inserts of the appropriate size and two different isolates, designated pSR2 and pSR6, were identified based on restriction patterns with enzymes other than EcoRV. The inserts from these two plasmids were used as probes against DNA from cosmid 4A-55 and transposon mutagenized cosmid DNA digested with EcoRV. These experiments indicated that the transposons had inserted into two different EcoRV fragments that were subcloned into the EcoRV site of pBS to produce pSR2 and pSR6. Thus, the region of interest spans these two fragments, indicating that the coding region for the gene of interest lies on the adjoining ends of these two fragments.

The nucleotide sequence of the two EcoRV fragments was determined with low to moderate accuracy to permit a survey of the entire coding capacity of the approximately 8 kb contained in the two fragments. This provided enough sequence information to distinguish a total of six open reading frames which were identified based on their sequence similarity to identified open reading frames deposited in GeneBank. One open reading frame was localized to the end of the EcoRV fragment used in the construction of pSR6, and the putative promoter region of the gene resided on the end of pSR2. This is in keeping with the previous finding that region of interest, delineated by the transposon insertions, spanned the two EcoRV fragments. Therefore, this open reading frame and its surrounding sequence was completely sequenced on both strands (SED ID No:1).

Figure 4:
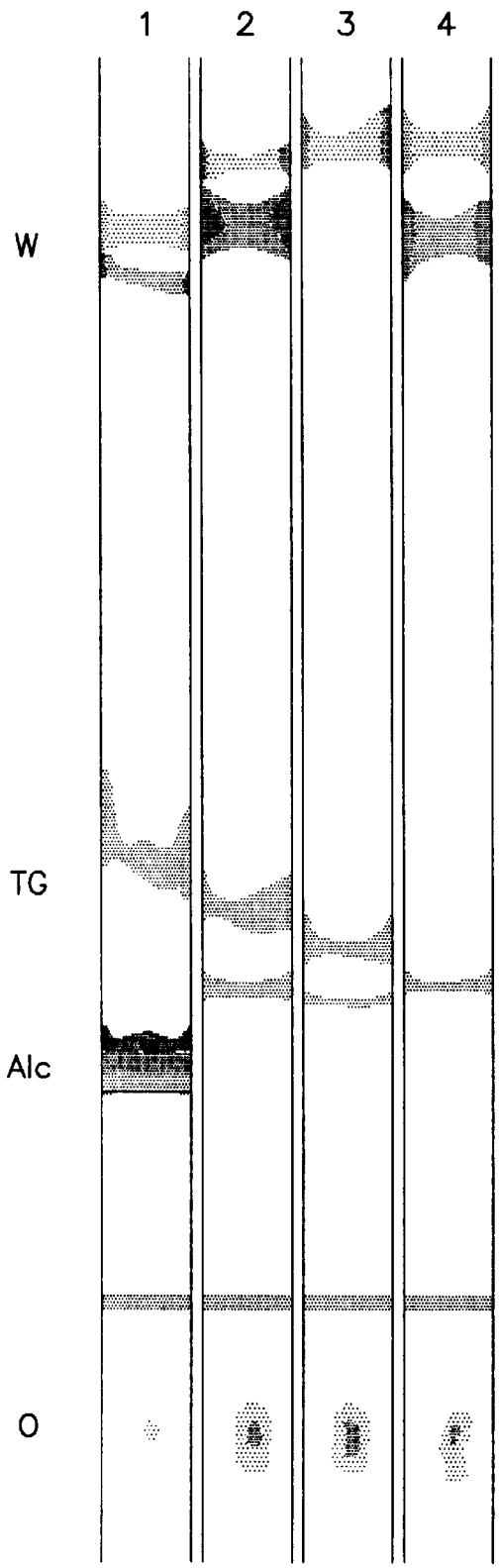
FIG. 4 TLC separation of lipid standards (lane 1) and neutral lipids extracted from *A. calcoaceticus* wild type (lane 2), the wow15 mutant (lane 3) and the wow15 mutant transformed with pSER2:acrl (lane 4). Symbols: W, wax esters, TG, triacylglycerol, Alc, hexadecanol, O, origin.

Examination of the open reading frame present in the gene sequence indicate that the largest protein, 32468 Daltons, would be encoded using GTG (Base pairs 358–360, SED ID No:1) as a translational initiation codon. For the sake of convenience we hitherto refer to this gene as the acr1 gene. Alignment of the acr1 ORF with the nucleic acid sequence is shown in FIG. 3. Use of GTG as an initiation codon is further supported by the presence of a conserved Shine Delgarno sequence of AGG from −10 to −13 bp (base pairs 346–349 of SEQ ID No:1) upstream of the predicted start site, while there is no such conserved sequence upstream of the first ATG codon (583–585 in SEQ ID No:1). The open reading frame predicted by the use of GTG as the translational initiation codon was subcloned by PCR from the complementary cosmid using oligonucleotide primers P5 and P6 (Table 3), which introduce BamHI sites at the ends of the amplified product. The amplified product was then subcloned into the BamHI site of pSER2 to give pSER2:acr1. This construct was used to transform E. coli strain DH5α for amplification and analysis, followed by subsequent transformation into the A. calcoaceticus, mutant wow15. Transformants were grown under wax inducing conditions, collected and extracted with chloroform/methanol for isolation of lipid compounds. Resolution of the lipid fraction by TLC indicated that wow15 transformed with pSER2:acr1 was now able to synthesize wax esters (FIG. 4), indicating that correct open reading frame had been identified, and that the gene responsible for the wow15 mutation had been cloned.

Comparison of the fully sequenced open reading frame identified from A. calcoaceticus with ORF2 of GenBank accession number U27357 from Mycobacterium tuberculo-sis resulted in an optimized FASTA score of 609 (FIG. 5) indicating a very strong similarity between the two proteins. ORF2 from M. tuberculosis was sequenced by Yuan et al. (1995) as part of an effort to characterize the cma1 gene encoding cyclopropane mycolic acid synthase. ORF2 is an open reading frame that is adjacent to cma1 on one side and on the other side to ORF3, an open reading frame with 35% identity (over 278 amino acids) to a trifunctional hydratase/dehydrogenase/epimerase from Candida topicalis which is involved in peroxisomal degradation of fatty acids. Based largely on this location between cma1 and ORF3, Yuan et al. (1995) concluded that the probable role of ORF2 was in some unidentified step of mycolic acid metabolism.

Based on the similarity between the amino acid sequence of the acr1 gene product and ORF2 from M. tuberculosis, we propose that ORF2 is a fatty acyl-CoA reductase. We consider it likely that this acyl-CoA reductase participates in the reductive condensation reaction in which the carboxy terminus of a substituted (i.e., methyl branched or cyclopropylated) long chain fatty acid is condensed with the α-carbon of a very long chain fatty acid. The carboxyl group of the substituted fatty acid is thought to become the β-hydroxyl of the mycolic acid. We propose that an intermediate step in this condensation reaction is the conversion by ORF2 of the carboxyl group of the substituted fatty acid to an aldehyde or an alcohol which then undergoes condensation with the α-carbon of a long chain fatty acid (i.e., typically a $C_{24}$ fatty acid)

EXAMPLE 3
Functional Expression of the Acyl-CoA Reductase in a Foreign Host

In this example the acyl-CoA reductase of this invention is expressed in a different bacterial species where it confers acyl-CoA reductase activity on the new host.

In vitro Reductase Activity Assays

To demonstrate this proposed enzymatic function of the acr1 gene product in vitro, and in order to teach the use of the gene for the production of acyl-CoA reductase activity in foreign bacterial hosts, the gene was subcloned into plasmid pET21. The acr1 gene was PCR amplified from the complementary cosmid using synthetic oligonucleotide primers P7 and P8 containing EcoRI and BamHI linkers for directional cloning (Table 3). The PCR product was gel purified, digested and subcloned into plasmid pET21 to produce plasmid pET21:acr1 which was used to transform E. coli strain BL21(DE3). In this expression system the gene is under the transcriptional control of a T7lac promoter which can be induced by the addition of IPTG. E. coli strain BD21(DE3) for expression studies was grown in LB medium with ampicillin (100 µg/ml). Three ml overnights were collected, washed and used to inoculate larger 50 ml cultures. When the cultures reached an optical density of 0.6 at 600 nm, they were induced to synthesize the protein of interest by adding IPTG to a final concentration of 1 mM. Cultures were allowed to grow for 2.5 hours before being collected and processed. To isolate the protein from cells containing pET21:acr1, or just pET21 as a control, cells were harvested by centrifugation at 5000×g for 10 minutes. Cells were resuspended in 500 mM sodium phosphate buffer (pH 7.4) and incubated 30° C. for 15 minutes in the presence 100µg/ml of lysozyme (Sigma). Cells were then sonicated for two 40 second bursts at maximum power. Soluble proteins were separated from cell walls and insoluble materials by centrifugation at 35,000×g for 30 minutes at 4° C. The soluble-fraction was collected as fraction I. The insoluble fraction was resuspended and resonicated as before. The sample was spun and the aqueous layer was collected fraction II. The resulting pellet was resuspended in a minimal amount of buffer to make a suspension as the insoluble fraction (fraction III). SDS-PAGE analysis of proteins was carried out using 12.5% homogeneous gels and protein was detected using silver staining.

Based on the sequence information for the acr1 gene (FIG. 3), it was predicted that the size of the induced protein should be approximately 32 kDa. Following induction of the system with IPTG, a protein of the predicted size was observed primarily in the insoluble protein fraction implying the protein is localized to the membrane, or is in the form of inclusion bodies.

Assays for acyl-CoA, acyl-ACP and palmitic acid reductase activity were conducted on all the protein fractions by incubating the extracts in the presence of $^{14}C$ labelled substrate. To test for enzymatic activity of the expressed protein from transformed *E. coli,* an assay was developed using radiolabelled palmitoyl-1-$^{14}$C-Coenzyme A (44.4 mCi/mmol, 30 μM final concentration, (NEN, Dupont)). Reactions were run in 30 μl volumes containing 167 mM sodium phosphate buffer (pH 7.4) in the presence of 100 mM NADPH and 13.5 μg of protein at 30° C. for 15 minutes. Components were added in the following order: water, buffer, NADPH, palmitoyl-1-$^{14}$C-coenzyme A and finally the protein. The assays were then extracted with 75 μl of chloroform:methanol (50:50), vortexed for 10 seconds and then centrifuged for 20 seconds for phase separation at maximum speed in a microfuge. The chloroform phase was then removed and spotted onto a TLC plate where the lipids were separated using a hexane:ethyl ether:acetic acid (90:10:1) solvent system. The TLC plate was then removed and allowed to dry before being exposed to a phosphorimaging cassette.

In order to determine if acyl-ACP was used as a substrate by acr1 gene product, it was necessary to synthesize this substrate from 1-$^{14}$C-palmitic acid and ACP using ACP synthase (a gift from Dr. Jan Jaworski, Miami University, Oxford Ohio). First the ammonium salt of palmitic acid was produced. Thirteen and a half microcuries (250 μl, 55.5 mCi/mmol, 3.54×10$^4$ dpm/μl) of 1-$^{14}$C-palmitic acid was dried down under nitrogen gas. It was then resuspended in 100 μl of 100% ethanol. Two drops of concentrated ammonia was added and the mixture was incubated at 65° C. for 5 minutes. This solution was then dried under nitrogen gas. The sample was then resuspended in 250 μl of 20% oxidant free triton X-100 and heated to 65° C. for 5 minutes.

Oxidant free triton X-100 was prepared in the following manner. One hundred microliters of triton X-100 was mixed into solution with 5 ml of 10 mM Tris-HCl, pH 8.0. NaBH$_4$ (100 mg) was added to the solution which was sealed in a teflon lined screw capped tube, shaken vigorously and incubated at 37° C. for 30 minutes. Concentrated HCl was added dropwise with vortexing until the addition of acid did not produce anymore foaming. The solution was then extracted twice with 2 ml of chloroform. The chloroform phases were dried down under nitrogen at 55° C. until there was no remaining smell of chloroform.

To synthesize the acyl-ACP, the following were combined in a screw cap microcentrifuge tube. Fifty microliters of 5× TML solution (0.5 M Tris-HCl (pH 8.0), 25 mM MgCl$_2$, 2 M LiCl), 5 μl of 0.1 M DTT, 12.5 μl of 0.1 M ATP (pH 7.6), 25 μl 20% oxidant free triton x-100 (described above), 25 μl of 1-$^{14}$C-palmitic acid (the ammonium salt, described above), 25 μl of acyl-ACP synthetase (a gift from Dr. Jan Jaworski), and 8 μg of ACP protein (Sigma) resuspended in 22.3 μl of 10 mM Tris-HCl (pH 8.0). This reaction mixture was incubated at 37° C. for 3 hours. At the end of the reaction the mixture was diluted 10× with H$_2$O to reduce the LiCl concentration.

A gravity flow column was prepared with a 100 μl bed of DEAE cellulose. The reaction was gently layered on top of the bed and allowed to gravity flow through the resin. The bed was then washed 4 times with 2 ml of wash solution (composed of the following for 100 ml total volume in ddH$_2$O, 80 ml isopropanol, 0.4 ml of 5 M NaCl, 0.2 ml of 1 M K$_2$HPO$_4$ (pH 6.0)). The bed was then washed with 2 ml of 50 mM Tris-HCl (pH 7.6). The column was then centrifuged to dryness at 1000 rpm in a table top centrifuge for 2 minutes. The sample was then eluted from the bed of the column by washing the cellulose four times, each time with 100 μl of 0.4 M LiCl in 50 mM Tris-HCl (pH 7.6). Between each application of the 100 μl of LiCl solution, the column was centrifuged for 2 minutes at 1000 rpm and the fraction collected. Ten microliter samples from each fraction were placed in scintillation fluid and the decays per minute counted. The first fraction was the most concentrated, at 1.26×10$^4$ dpm per 10 μl. The total counts for the entire volume collected measured 2.66×10$^4$. A total of 1.0×10$^4$ dpm (approximately 5.6×10$^{-4}$ μmol of labelled acyl-ACP) of fraction 1 was used for each reaction testing for acr1 activity from the *E. coli* protein extracts as described above for the assays in which acyl-CoA was the substrate.

Figure 6:
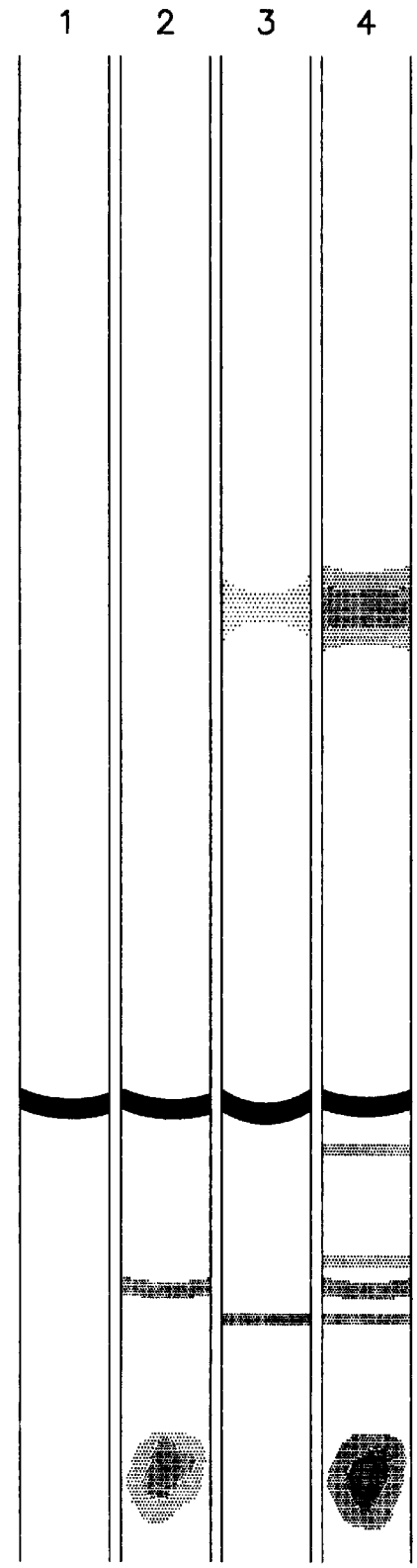
FIG. 6 Phosphorimage of TLC plate showing the products from acyl CoA reductase enzyme assays in which the source of protein extract was the soluble (lane 1) or insoluble (lane2) fraction from extracts of *E. coli* containing the vector pET21, or soluble (lane 3) or insoluble (lane 4) fraction from *E. coli* containing pET:acrl. Symbols, FA, fatty aldehyde; Alc, fatty alcohol.

The greatest amount of enzymatic activity (i.e., acyl-CoA reductase activity) was associated with the insoluble fraction where the induced protein was observed to be localized (FIG. 6). Additionally, enzymatic activity was only observed in the presence of acyl-CoA, implying the enzyme is specific for this substrate. Experiments aimed at determining the cofactor specificity of the enzyme showed that catalytic activity was observed when the enzyme was incubated in the presence of NADPH and not NADH. Production of $^{14}$C labelled fatty alcohol was also observed in assays of protein extracts from *E. coli* transformed with pET21:acr1. However, it was subsequently found that *E. coli* contains an endogenous activity that is capable of converting fatty aldehyde to fatty alcohol.

Although this example specifically teaches production of the acyl-CoA reductase in *E. coli* cells, it will be obvious to one skilled in the art that similar procedures can be used to express the acyl-CoA reductase in cells of many other bacterial species. including cyanobacteria, for which transformation methods and vectors are available. It is additionally envisioned that by the use of other plasmid vectors and methods, it will be possible to express the acyl-CoA reductase gene of this invention in fungi, yeast and plant cells. Expression of the gene in plant cells is especially preferred because of the low cost of production of fatty acids from many plant species. Thus, it is expected that expression of the acyl-CoA reductase of this invention under transcriptional control of a promoter that is highly expressed in developing seeds of oilseed species such as canola, rapeseed, soybean, sunflower, safflower, peanut, crambe, *Brassica juncea* and others will lead to conversion of acyl-CoA molecules to fatty aldehydes. The metabolic fate of the fatty aldehydes in developing seeds is not known. However, when expressed in conjunction with genes encoding fatty aldehyde reductase and fatty acyl-CoA: fatty alcohol acyltransferase (wax synthase of U.S. Pat. No. 5,445,947) it is expected that the combined action of the three enzymes will lead to production of wax esters that will be accumulated by the developing seeds in the same way that other neutral lipids (eg., triacylglycerols) are stored in these tissues. It is also possible that the fatty aldehydes will accumulate in the oil bodies of developing oilseeds as fatty aldehydes. It is also possible that some plants have enzymes that will modify the aldehyde group by reduction to the alcohol, acetylation, methylation or other modifications that will facilitate storage of the fatty aldehyde or a derivative in the oil bodies.

EXAMPLE 4

Isolation of a Fatty Acyl-CoA Reductase from *Mycobacterium tuberculosis*.

Comparison of the fully sequenced open reading frame identified from *A. calcoaceticus* with the polypeptide sequences in public databases was accomplished by using the BLAST algorithm provided via the world wide web by the National Center for Biotechnology Information at URL http://www.ncbi.nlm.nih.gov/. The sequence of the *A. calcoaceticus* gene product showed highly significant sequence homology to a previously sequenced gene from *Mycobacterium tuberculosis* (ORF2 of GenBank accession number U27357). The use of the FASTA algorithm to align the two sequences resulted in an optimized FASTA score of 609 (FIG. 5) indicating a very strong similarity between the two proteins. ORF2 from *Mycobacterium tuberculosis* was sequenced as part of an effort to characterize cma1, a gene encoding cyclopropane mycolic acid synthase. ORF2 is an open reading frame that resides just downstream of cma1. Based on this location between cma1 and ORF3, an open reading frame with 35% identity (over 278 amino acids) to a trifunctional hydratase/dehydrogenase/epimerase from *Candida topicalis* which is involved in peroxisomal degradation of fatty acids, Yuan et. al. (1995) concluded that the probable role of ORF2 was in mycolic acid metabolism.

Based on the homology between ORF2 and the acyl-CoA reductase of this invention, we envision that ORF2 is an acyl-CoA reductase that is involved in the synthesis of mycolic acid. This prediction may be confirmed by cloning the gene from *M. tuberculosis* into pET21 essentially as described above, introducing the gene into *E. coli* and assaying for enzyme activity as described above. The function may also be demonstrated by the ability of ORF2 to functionally complement the wow15 mutation as described above for the acr1 gene. In view of the observation that some acyl CoA reductases may have strict substrate specificity, we consider it possible that the ORF2 gene product will exhibit a different substrate specificity than the acr1 gene product. In particular, the ORF2 gene product is expected to act on acyl-CoA esters of very long chain fatty acids of approximately 36 carbons.

The sequence identity between ORF2 and the acr1 gene provides useful information on the design of nucleic acid primers and probes for the isolation of other bacterial acyl-CoA reductase genes. In a preferred embodiment, synthetic oligonucleotide primers based on the following regions of amino acid sequence are expected to be most useful in identifying such genes by any of the various methods used to clone related genes. The following regions from SEQ ID No:2 would be most useful: residues 20–29, 100–108, 127–133, 198–206. A preferred method would involve the use of mixed oligonucleotides of approximately fourteen or more nucleotides that encode all possible codons corresponding to a region of the indicated amino acid sequences. These mixed oligonucleotides are used to prime PCR reactions in which genomic DNA from a bacterium is used as the template and the general condition of the reaction are those employed by Gould et al. (1989). As shown by Gould et al. (1989), oligonucleotides with as Much as several hundred thousand-fold ambiguity can be used to obtain the correct amplification products. Any products obtained by this method would be cloned and sequenced to verify the presence of additional regions of sequence identity between the amplified fragment and the acyl-CoA reductase of this invention. The fragment would then be used to obtain a full length genomic clone from the source organism. The function of the full length clone would then be verified by expressing it in *E. coli* and assaying for enzyme activity as shown in the foregoing example.

EXAMPLE 5

Identification of a Fatty Acyl-CoA Reductase from Higher Plants

The sequence of the acyl-CoA reductase of this invention has been used to identify two cDNAs from a higher plant that exhibits significant sequence similarity. GenBank accession numbers T21872 and Z27263 correspond to partial cDNA sequences from *Arabidopsis thaliana* that were obtained by partial sequencing of random anonymous cDNA clones. Thus, although the sequence of these genes are publicly available, the function of the corresponding gene products are not generally known. An alignment of part of the amino acid sequence of the *A. calcoaceticus* acr1 gene and the deduced amino acid sequence of the partial cDNA sequences of the *A. thaliana* clones are shown in FIG. 7 and FIG. 8. Analysis with the FASTA algorithm indicates that acr1 and T21872 are 25.8% similar over a region of 97 amino acids, corresponding to an optimized FASTA score of 97. Similarly, analysis with the FASTA algorithm indicates that acr1 and Z27263 are 32.9% similar over a region of 85 amino acids, corresponding to an optimized FASTA score of 85. Thus, we envision that the gene products corresponding to T21872 and Z27263 catalyze acyl-CoA reductase activity. These genes may be used to identify homologous plant genes from plant species of commercial interest by methods familiar to one skilled in the art as outlined above.

All higher plants contain acyl-CoA reductases that are involved in the synthesis of fatty alcohols as constituents of epicuticular wax. Thus, we envision that T21872 and Z27263 encode plant acyl-CoA reductases that participate in synthesis of cuticular fatty alcohols, a constituent of epicuticular 'wax'. The plant genes should be useful in modifying the amount or composition of plant waxes. The composition of plant waxes has been implicated in susceptibility to infection with bacterial and fungal pathogens and predation by leaf insects. Also, wax composition and amount is thought to be important in preventing excessive water loss from plants. Thus, the Arabidopsis gene and homologous genes from other plants may be used to alter the composition and amount of wax by increasing or decreasing the level of expression of the corresponding gene in transgenic plants by methods, such as obtaining high level expression from strong promoters or suppressing expression with antisense, that are known to those skilled in the art. Decreases in the amount of wax constituents may be of value in those cases where a constituent attracts pathogens or pests or when the constituent is a contaminant of some product obtained from the plant. For example, wax in the husks of sunflower seeds is a problematic contaminant during the pressing of oil from sunflower seeds.

The function of the anonymous cDNA clones T21872 and Z27263 may be established by mapping the genes on the Arabidopsis genome and testing whether they corresponds to any of the 21 different mutations that are known to alter wax composition in Arabidopsis. If the genes map near a mutation, a full length cDNA or a genomic clone could be introduced into the mutant to determine if it complements the mutation. Complementaton of a missing enzymatic function would establish the identity of the gene. In addition, the cDNAs, or fragments thereof, may be introduced in an antisense orientation under transcriptional control of the cauliflower mosaic virus 35S promoter or other promoters into wild type Arabidopsis plants by Ti plasmid-mediated transformation. It is anticipated that in a small proportion, roughly 5%, of the transgenic plants, the expression of the antisense version of the gene will cause a strong reduction in expression of the endogenous gene with a corresponding diminution of the endogenous enzyme activity from the gene product. Transgenic plants with reduced levels of sense mRNA for the gene may be identified by preparing northern blots on mRNA from the transgenic plants probed with the cDNA. Plants in which the amount of sense mRNA is reduced below about 10% of normal levels will be analyzed for wax composition. Briefly, this involves extracting wax from the leaves and stems by dipping tissues in chloroform. The chloroform extract is usually concentrated by evaporation and the resulting waxes are then analyzed by gas chromatography and mass spectrometry and identified by reference to standards of known composition. We anticipate that, in the present case, antisense suppression of the acyl-CoA reductase-like genes from Arabidopsis will result in a decrease in the amount of one or more fatty alcohols, aldehydes or wax esters.

References cited herein are listed below for convenience and are hereby incorporated by reference.

REFERENCES

Altschul, S. F., Gish, W., Miller, W., Myers, E. W., Lipman, D. (1990) Basic local alignment search tool. *J. Mol. Biol.* 215: 403–410.

Dewitt, S., Ervin, J. L., Howes-Orchison, D., Dalietos, D., and Neidleman, S. L. 1982. Saturated and unsaturated wax esters produced by Acinetobacter sp. H01-N grown on $C_{16}$–$C_{20}$ n-alkanes. *J. Am. Oil Chem. Soc.* 59: 69–74.

Doolittle, R. F., (1986) of Urfs and Orfs, University Science Books, Mill valley, Calif. pp. 12

Fixter, L. M., Nagi, M. N., McCormack, J. G. and Fewson, C. A. 1986. Structure, distribution and function of wax esters in *Acinetobacter calcoaceticus. J. Gen. Micro.* 132: 3147–3157.

Fox, M. G. A., Dickinson, M. and Ratledge, C. 1992. Long-chain alcohol and aldehyde dehydrogenase activities in *Acinetobacter calcoaceticus* strain H01-N. *J. Gen. Micro.* 138:1963–1972.

Gould, S. J., Subramani, S., Scheffler, I. E. (1989) Use of the DNA polymerase chain reaction for homology probing. *Proc. Natl. Acad. Sci. USA* 86: 1934–1938.

Hunger, M., Schmucker, R., Kishan, V. and Hillen, W. 1990. Analysis and nucleotide sequence of an origin of DNA replication in *Acinetobacter calcoaceticus* and its use for *Escherichia coli* shuttle plasmids. Gene 87: 45–51.

Kleckner, N., Bender, J. and Gottesman, S. 1991. Uses of Transposons with Emphasis on Tn10. In *Methods of Enzymology: Bacterial Genetic Systems.* Vol. 204. Miller, J. H. (ed.). Academic Press Inc., San Diego, Calif.

Maniatis, T., Fritsch, E. F., and Sambrook, J.. 1982. In *Molecular Cloning, A Laboratory Manual.* Cold Spring Harbor Laboratory Press, New York, N.Y.

Metz, J. G., Lardizabal, K. D., and Lassner, M. W. 1995. Calgene Inc. U.S. Pat. No. 5,445,947. Jojoba wax biosynthesis gene. Filed May 20, 1993, awarded Aug. 29, 1995.

Pollard, M. R. and Metz, J. G.. 1995. Calgene, Inc. U.S. Pat. No. 5,411,879. Fatty acyl reductases. Filed Nov. 8, 1993, awarded May 2, 1995.

Singer, M. E. and Finnerty, W. R. 1985. Alcohol dehydrogenases in Acinetobacter sp. Strain H01-N: Role in hexadecane and hexadecanol metabolism. *J. Bacteriol* 164: 1017–1024.

Shanklin, J. and Somerville, C. R. 1991. Stearoyl-ACP desaturase from higher plants is structurally unrelated to the animal homolog. Proc. Natl. Acad. Sci. USA 88: 2510–2514

Singer, M. E. and Finnerty, W. R.. 1985c. Fatty aldehyde dehydrogenases in Acinetobacter sp. Strain H01-N: Role in hexadecane and hexadecanol metabolism. *J. Bacteriol.* 164: 1011–1016.

Yuan, Y., Lee, R. E., Besra, G. S., Belisle, J. T. and Barry, C. E. 1995. Identification of a gene involved in the biosynthesis of cyclopropanated mycolic acids in *Mycobacterium tuberculosis. Proc. Natl. Acad. Sci. USA.* 92:630–6634.

What is claimed is:

1. An isolated nucleic acid fragment encoding a polypeptide having acyl-CoA reductase activity and having a nucleotide sequence at least about 60% similar to SEQ ID NO:1.

2. The isolated nucleic acid fragment of claim 1 which has a nucleotide sequence at least about 80% similar to SEQ ID NO:1.

3. The isolated nucleic acid fragment of claim 2 having the nucleotide sequence of SEQ ID NO:1.

4. A recombinant DNA construct comprising a nucleic acid fragment encoding a polypeptide having acyl-CoA reductase activity and having a nucleotide sequence at least about 60% similar to SEQ ID NO:1.

5. The recombinant DNA construct of claim 4 wherein said nucleotide sequence is at least about 90% similar to SEQ ID NO:1.

6. The recombinant DNA construct of claim 5 wherein said nucleotide sequence is at least about 95% similar to SEQ ID NO:1.

7. The recombinant DNA construct of claim 6 wherein said nucleotide sequence is SEQ ID NO:1.

8. A recombinant DNA construct comprising a nucleic acid fragment encoding the polypeptide of SEQ ID NO:2.

9. A host cell comprising the recombinant DNA construct according to claim 5.

10. The host cell of claim 9 which is a bacterial cell.

11. The host cell of claim 10 which is *E. coli*.

12. The host cell of claim 9 which is a plant cell.

13. A method of producing a bacterial acyl-CoA reductase, or products of said reductase, by recombinant DNA methods comprising culturing or growing the host cells of claim 9 under conditions such that expression of the reductase occurs.

14. The method of claim 13 wherein said host cell is a bacterial cell.

15. The method of claim 14 wherein said host cell is a plant cell.

16. The method of claim 13, further comprising recovering a fatty alcohol, an aldehyde or a wax ester from said culture.

* * * * *